(12) United States Patent
Dakin et al.

(10) Patent No.: US 6,368,326 B1
(45) Date of Patent: *Apr. 9, 2002

(54) INTERNAL CORD FIXATION DEVICE

(75) Inventors: Edward B. Dakin, Lindsay (CA); Albert L. Lippincott, III, Prior Lake, MN (US)

(73) Assignee: Daos Limited (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/162,036

(22) Filed: Sep. 28, 1998

(51) Int. Cl.[7] ................................................ A61B 17/58

(52) U.S. Cl. ........................ 606/103; 606/71; 606/73; 606/74; 606/232

(58) Field of Search ................................ 606/103, 139, 606/150, 232, 73, 71, 213, 74, 60; 411/340; 623/13.14, 13.19, 13.2

(56) References Cited

U.S. PATENT DOCUMENTS

| | | | |
|---|---|---|---|
| 887,074 A | 5/1908 | Depage | |
| 2,143,922 A | * 1/1939 | Longfellow | .................. 606/103 |
| 2,501,978 A | 3/1950 | Wichman | |
| 3,477,429 A | 11/1969 | Sampson | |
| 3,709,218 A | 1/1973 | Halloran | |
| 3,997,138 A | 12/1976 | Crock et al. | |
| 4,041,939 A | 8/1977 | Hall | |
| 4,047,523 A | 9/1977 | Hall | |
| 4,050,464 A | 9/1977 | Hall | |
| 4,120,298 A | 10/1978 | Fixel | |
| 4,146,022 A | 3/1979 | Johnson et al. | |
| 4,492,226 A | 1/1985 | Belykh et al. | |
| 4,587,963 A | 5/1986 | Leibinger et al. | |
| 4,708,132 A | 11/1987 | Silverstrini | |
| 4,790,303 A | 12/1988 | Steffee | |
| 4,889,110 A | 12/1989 | Galline et al. | |
| 4,976,712 A | 12/1990 | Vanderslik | |
| 4,976,740 A | 12/1990 | Kleiner | |
| 5,013,314 A | 5/1991 | Firica et al. | |
| 5,108,397 A | 4/1992 | White | |
| 5,116,340 A | 5/1992 | Songer et al. | |
| 5,156,616 A | 10/1992 | Meadows et al. | |
| 5,201,733 A | 4/1993 | Etheredge, III | |

(List continued on next page.)

FOREIGN PATENT DOCUMENTS

| | | | |
|---|---|---|---|
| DE | 1958429 | 7/1971 | |
| EP | 0298400 | 1/1989 | |
| EP | 576337 | * 6/1993 | .................. 606/232 |
| WO | WO 98 11838 | 3/1998 | |

OTHER PUBLICATIONS

Acumed, Inc. Osteo–Clage Cerclage Cable Systemss, Jul. 1992.

(List continued on next page.)

*Primary Examiner*—David O. Reip
*Assistant Examiner*—Julian W Woo
(74) *Attorney, Agent, or Firm*—Fredrikson & Byron, P.A.

(57) ABSTRACT

Methods and apparatuses for fixing a bone fragment or a bone prosthesis onto a bone. To affix a bone fragment to the bone, an internal fastener is attached from within the interior of the bone to a bone fragment with a length of flexible, inelastic cord extending within the bone interior and attached to the fastener and passing outwardly through an opening in a second bone fragment. The fastener and cord are so positioned as to draw respective fracture surfaces together to reduce the fracture when the cord is pulled outwardly of the opening in the second bone fragment. A second fastener desirably is attached to the bone opening, this fastener including an open bore to receive the cord and a lock to secure the cord to this fastener and maintain the cord under tension.

17 Claims, 20 Drawing Sheets

U.S. PATENT DOCUMENTS

| | | | | |
|---|---|---|---|---|
| 5,306,290 | A | * | 4/1994 | Martins et al. ............. 606/232 |
| 5,312,410 | A | | 5/1994 | Miller et al. |
| 5,324,291 | A | | 6/1994 | Ries et al. |
| 5,395,374 | A | | 3/1995 | Miller et al. |
| 5,449,361 | A | | 9/1995 | Preissman |
| 5,454,812 | A | | 10/1995 | Lin |
| 5,474,554 | A | | 12/1995 | Ku |
| 5,536,270 | A | | 7/1996 | Songer et al. |
| 5,562,668 | A | | 10/1996 | Johnson |
| 5,569,253 | A | * | 10/1996 | Farris et al. .................. 606/74 |
| 5,571,139 | A | | 11/1996 | Jenkins, Jr. |
| 5,611,801 | A | * | 3/1997 | Songer ........................ 606/73 |
| 5,720,765 | A | * | 2/1998 | Thal ........................... 606/232 |
| 5,788,697 | A | * | 8/1998 | Kilpela et al. ................ 606/74 |
| 5,797,913 | A | * | 8/1998 | Dambreville et al. ....... 606/103 |
| 5,921,986 | A | * | 7/1999 | Bonutti ....................... 606/60 |
| 6,068,648 | A | * | 5/2000 | Cole et al. .................. 606/232 |

OTHER PUBLICATIONS

Howmedica The Dall–Miles Cable Grip System, 1995.

Zimmer Cable–Ready Cable Grip System, Aug. 1994.

Mears D.C., Shirahama M., Stabilization of an Acetabular Fracture With Cables for Acute Total Hip Arthroplasty, The Journal of Arthroplasty, vol. 13, No. 1, 1998, pp. 104–107.

Labitzke R. Von der "Knochennacht" zu zeitgenossischen Osteosyntheseneine Chronologie, Chirurg (1995) 66: pp. 452–458.

Dall D.M., Miles A.W. Re–attachment of the Greater Trochanter The Use of the Trochanter Cable–Grip System, JBJS (British), vol. 65–B, No. 1, Jan. 1983, pp. 55–59.

Labitzke R., Schramm G., Witzel U., Quisthout P. "Sleeve–Rope Closure" of the Median Sternotomy after Open Heart Operations, Thorac. cardiovasc. Surgeon 31 (1983). pp. 127–128.

Labitzke R., Drahtseile und intraossare Druckverteilungschulsenin der Chirurgie, Chirurg 53: (1982). pp. 741–743.

Labitzke R., Towfigh H. Operationstechnik und behandlungsergebnisse nach lateraler Zuggurtung an Patella und Olecranon, Unfallheilkunde 83, (1980), pp. 450–456.

Meeder P.J., Wentzensen A., Weise K. Die operative Behandlung der frischen acromio–clavicularen Luxation (Tossy III) durch Naht der Ligamente und Kirschner–Drahtzuggurtung, Langenbacks Arch. Chir. 350, (1980), pp. 169–173.

Schweiberer Von L. Operative Behandlung von Patellafrakturen, Zentralblatt fur Chirurgie, 1977, Heft 16, pp. 982–987.

Labitzke R. Die laterale Zuggurtung, Arch. orthop. Unfall–Chir. 81, (1975), pp. 193–198.

Labitzke R. Statisch–experimentelle Untersuchungen zur Zuggurtun (dargestellt an der Olecranofraktur) Mschr. Unfallheilk. 78, (1975), pp. 393–400.

Labitzeke R. Uberlegungen zur Theorie der Zuggurtung, Arch. orthop. Unfall–Chir. 81, (1975), pp. 179–192.

Labitzke R. Bipolar interfragmentare Druckkraftmessung am Modellknochen bei Variierung der Zuggurtung einer Olecranonfraktur, Arch. orthop. Unfall–Chir. 81, (1975), pp. 199–205.

Labitzke R., Rehn J. Zur Behandlung von Patellafrakturen, Arch orthop. Unfal–Chir. 77, (1973), pp. 64–74.

Latizke R, Kehr H, Rehn J. Zur Behandlung von Olecranon–Frakturen und Olecranon–Pseudarthrosen, Arch. orthop. Unfall–Chir. (1972), pp. 247–256.

* cited by examiner

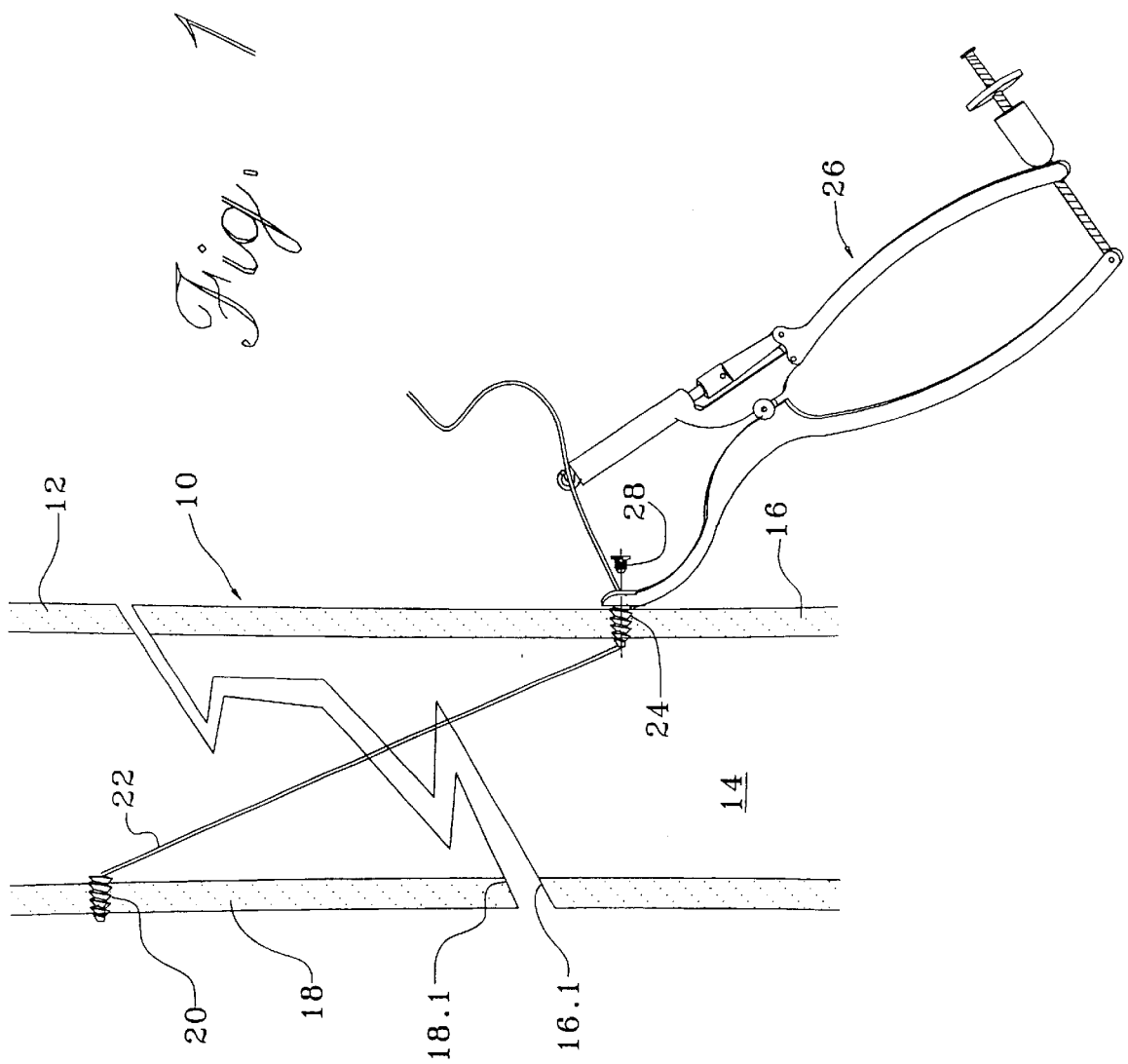

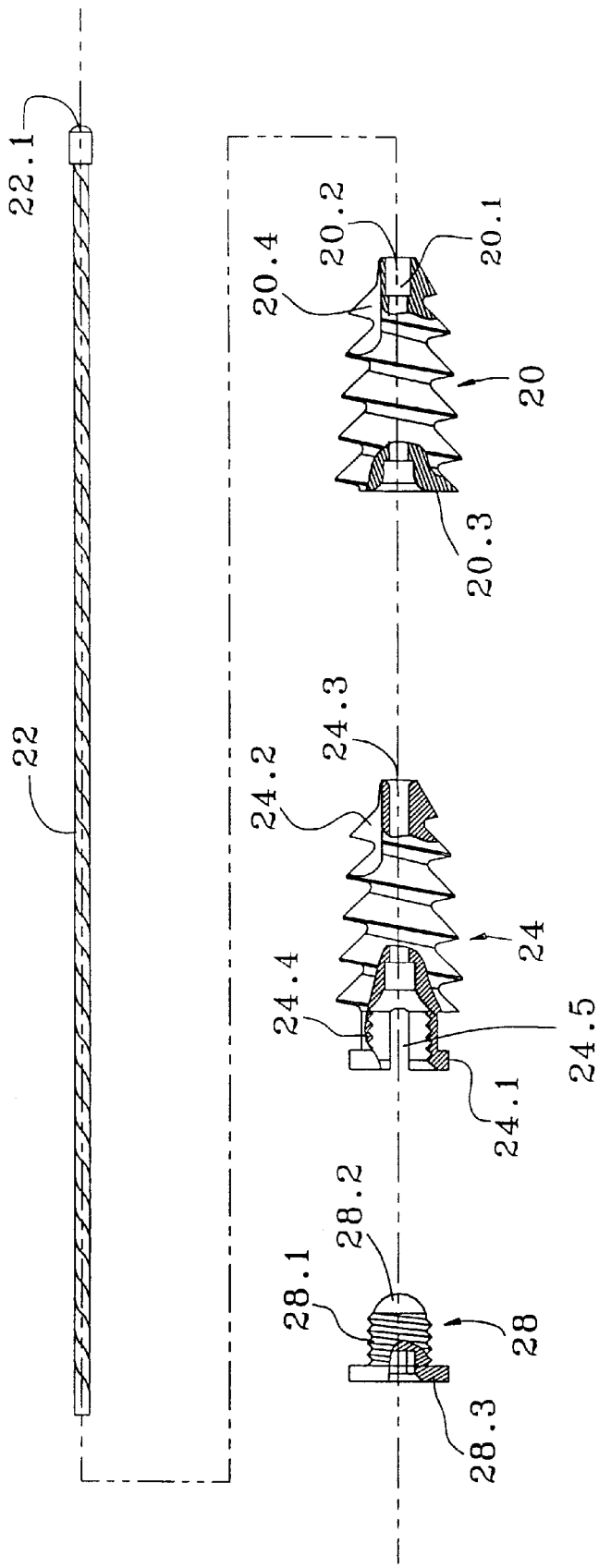

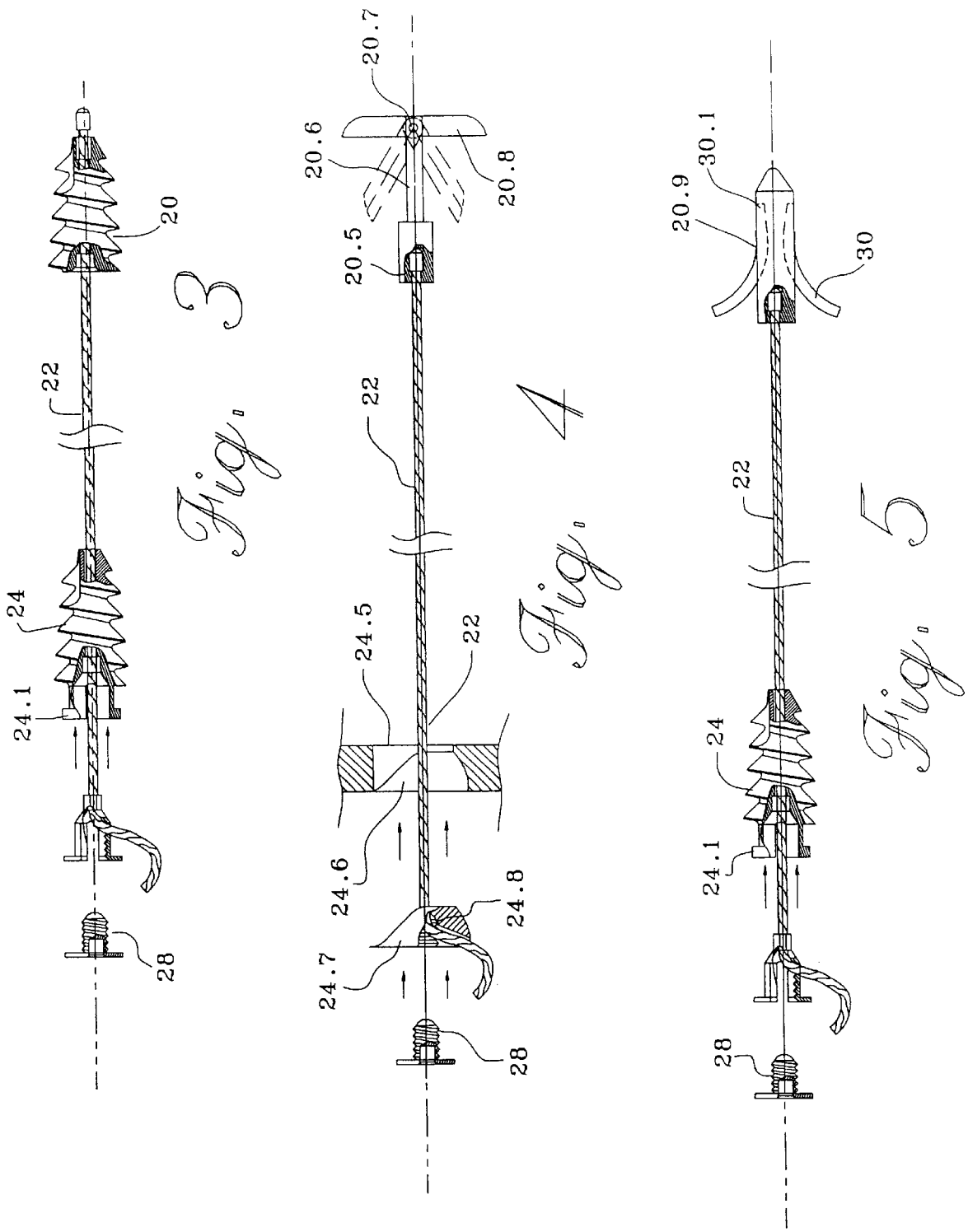

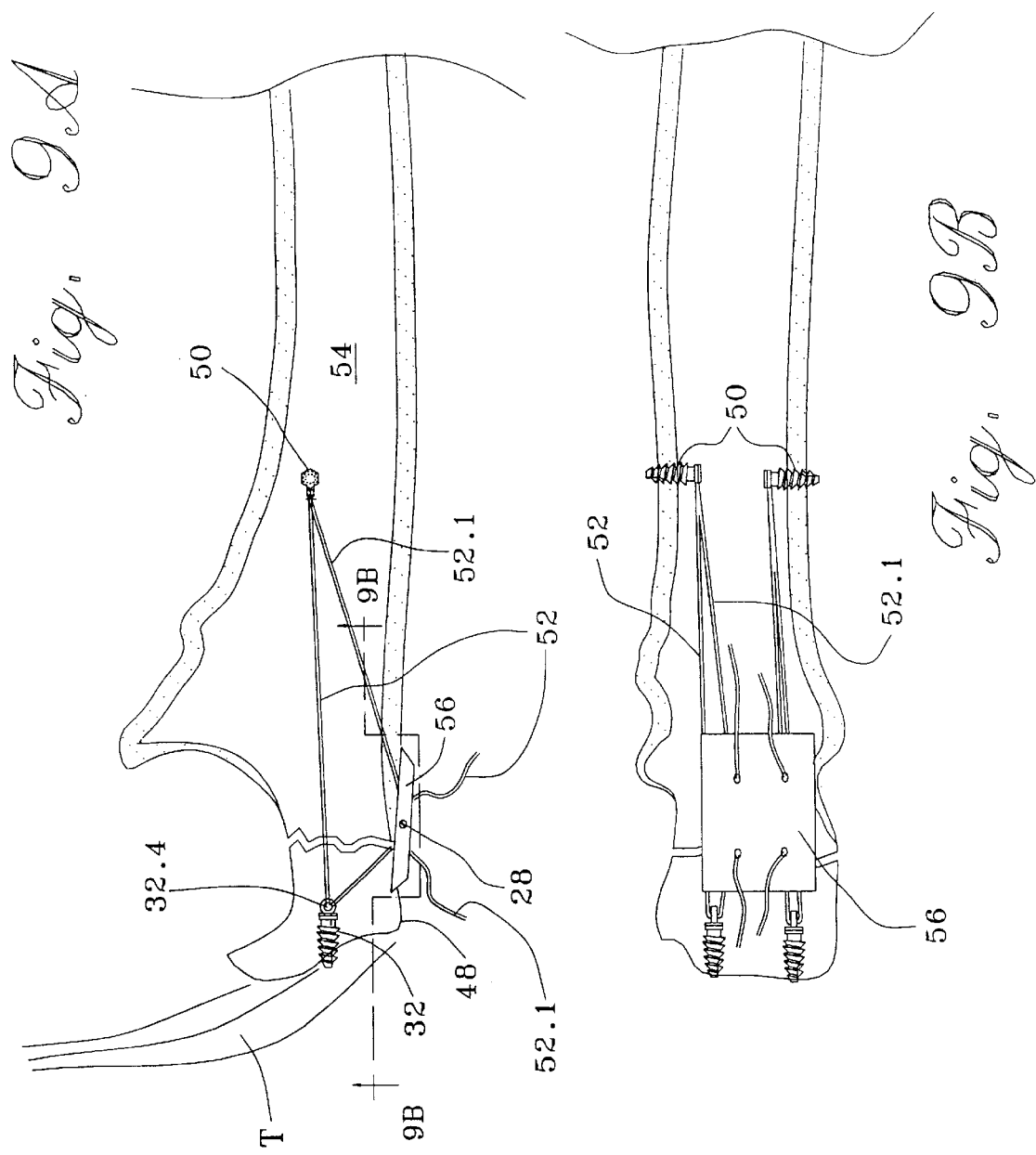

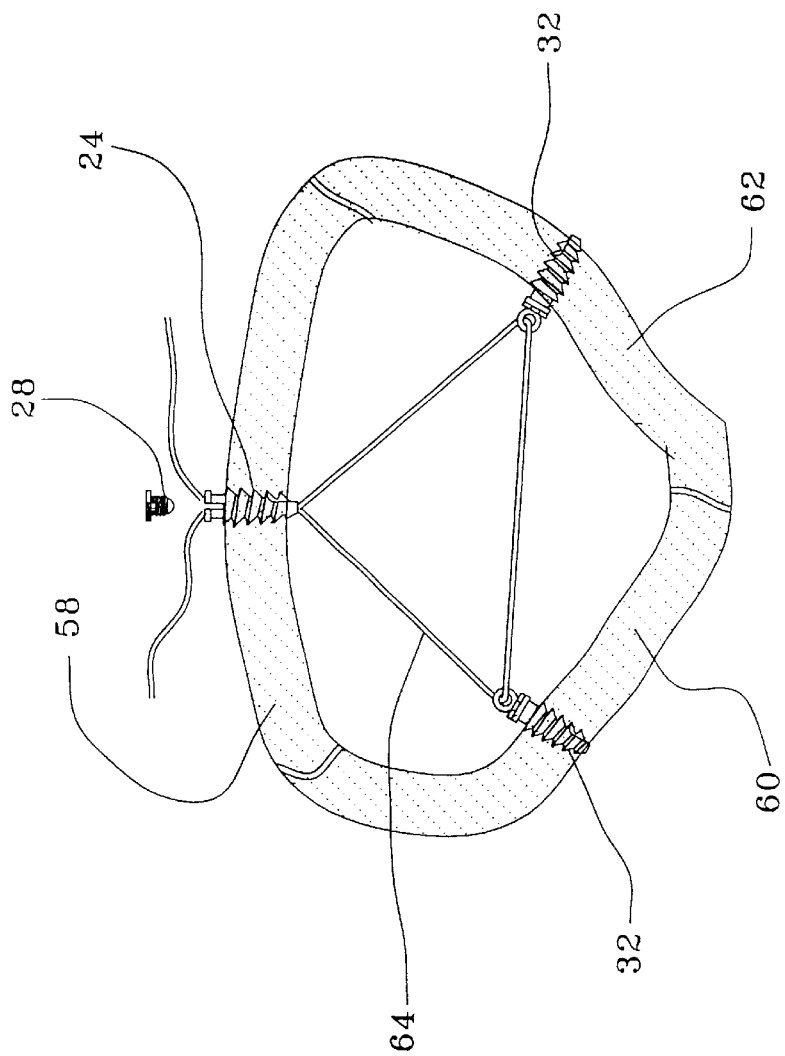

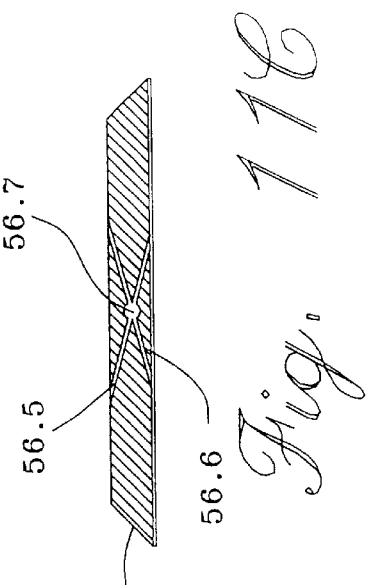
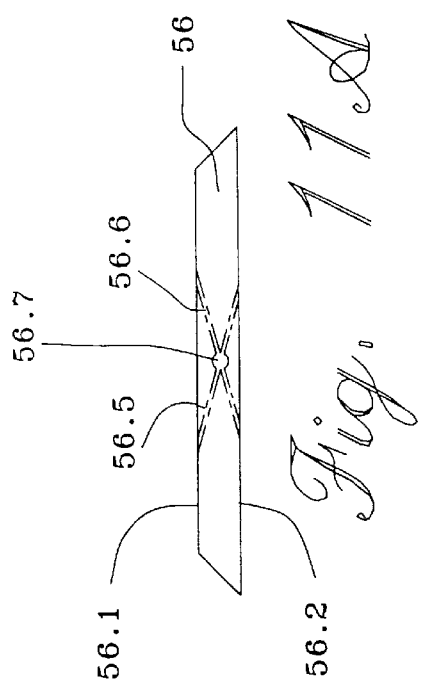
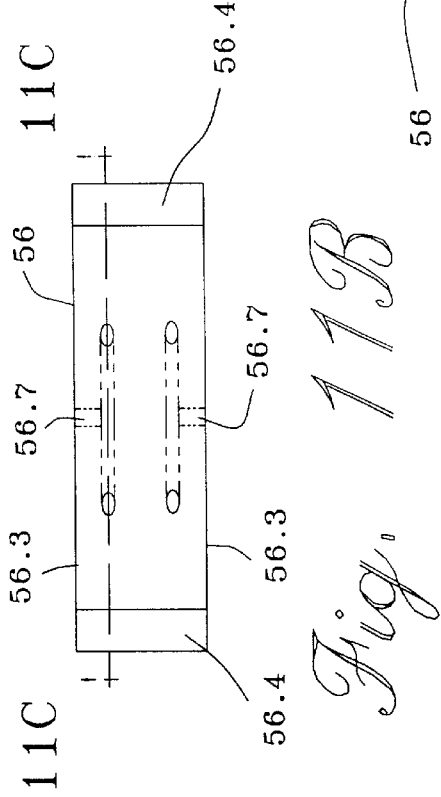

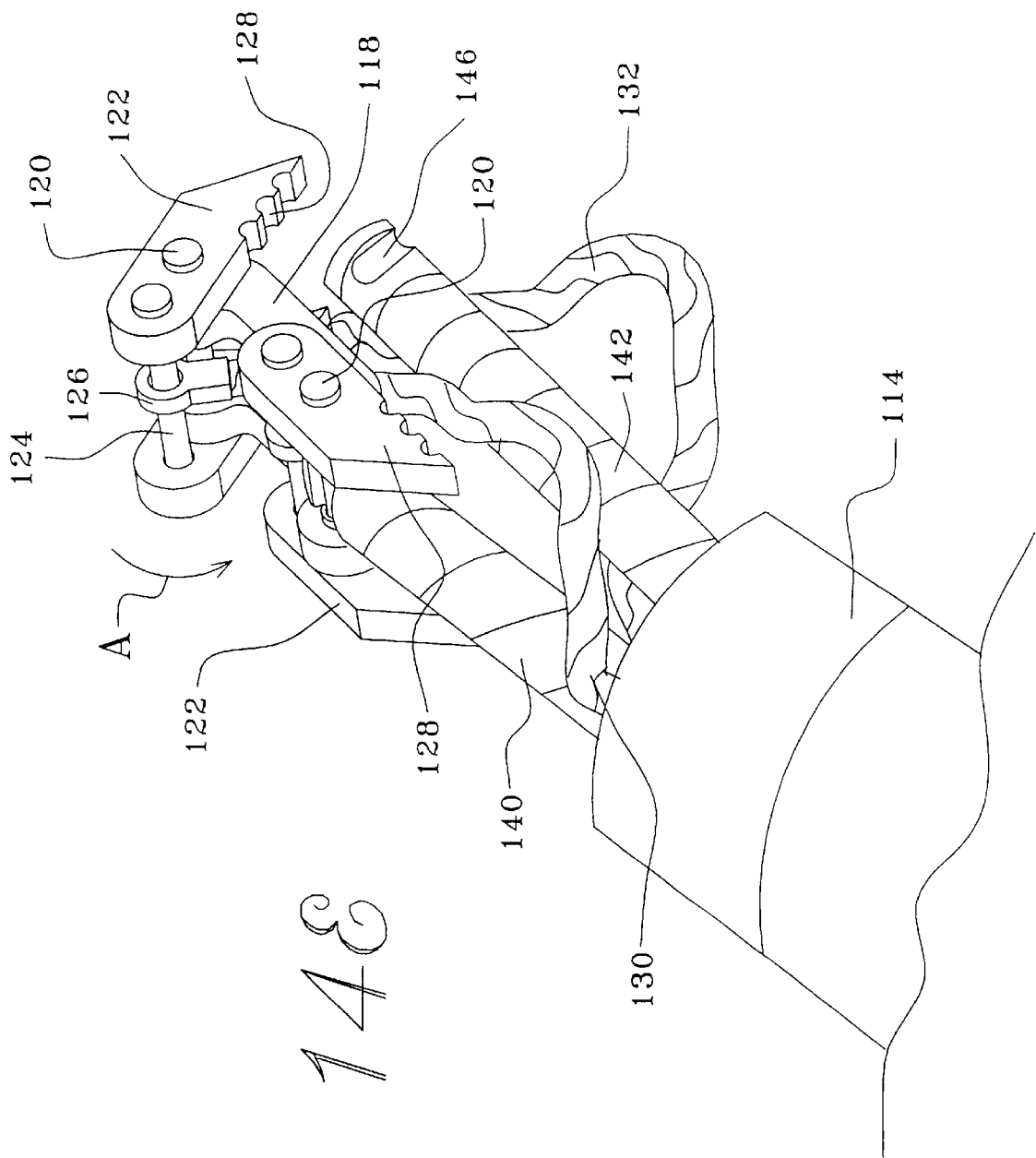

INTERNAL CORD FIXATION DEVICE

FIELD OF THE INVENTION

This invention pertains to the field of fixation devices for bones.

BACKGROUND OF THE INVENTION

Simple fractures of bones are readily treated by bringing the fracture surfaces together and holding them in the desired orientation with respect to one another through the use of splints, casts and the like. Bones in general have dense outer, strong cortical portions and interior, non-cortical portions that may include cancellous bone.

Comminuted fractures and fractures involving the breakage of a bone into numerous bone fragments are more difficult to deal with since one must attempt to reposition each bone fragment in an orientation relative to each other bone fragment so that the fragments may knit together properly. For this purpose, physicians have often used metal plates that attach to the outer cortical surfaces of the bones and which utilize bone screws to hold the bone fragments in position.

Another method involves the use of cerclage procedures in which a wire is, in effect, wrapped about a broken bone to hold the fragments in place, the cerclage wire occasionally penetrating through the bone. Reference is made to Johnson et al., U.S. Pat. No. 4,146,022. Yet another method taught in Berger, U.S. Pat. No. 5,658,310, involves anchoring the balloon portion of a balloon catheter in the medullary cavity at one end of a long bone having a transverse fracture, and stretching the remaining portion of the elastic catheter across the fracture interface within the bone to maintain the fracture interface in compression. It would appear that unless the elastic catheter traverses the precise center of the bone at the fracture site (which may be difficult to accomplish, considering the bowed or curved nature of most bones), compressive forces will be uneven across the fracture site. That is, the compressive forces on the side of the bone nearest the catheter will be greater than the compressive forces on the opposite side of the bone, generating an unwanted bending moment across the fracture site.

Surgical procedures used to mount bone plates and cerclage elements to a bone often require supportive tissue that is normally joined to the bone to be cut from the bony tissue to enable direct visual access to the bone. With cerclage procedures, one must entirely encircle a bone in order to hold the bony parts together.

Procedures using bone plates and cerclage elements often tend to interrupt blood flow to the damaged bone fragments, and thus hinder the healing process. Moreover, the use of bone plates and cerclage elements, particularly the former, can lead to stress shielding of the fracture site. It is well known (Wolff's law) that bone growth is stimulated when stress is applied. However, continuous, excessive pressure applied to a bone may cause unwanted resorption of bone at the pressure site. In order to promote healing of bone fractures, the fracture surfaces that are brought together during reduction of the fracture should be subject to cyclic or periodic compressive forces so as to stimulate the growth of new bone across the fracture interface without causing bone resorption. When a fracture interface is immobilized, as by a cast, the bone material that is deposited at the fracture interface may have a collagen fiber matrix that is random rather than aligned with the fiber matrix of bone on either side of the fracture, the healed fracture interface being weaker in tension than bone on either side of the interface.

Some bone fractures result in the production of many bone fragments, and proper reduction of the fracture requires the fragments to be carefully reassembled next to each other with their fracture surfaces in contact. Bone screws and bone plate devices commonly are used for this purpose. Using bone screw techniques, two bone fragments may be joined together, and these two fragments as a unit may be moved into approximation with a third fragment and joined to it, and so on. Fragments that are thus joined together by rigid screws cannot move with respect to other fragments, and mismatching of the fracture surfaces as the first several fragments are joined together can have a compounding effect, causing mal-union or non-union of fracture surfaces and resulting in far less than perfect bone fragment assembly and healing.

SUMMARY OF THE INVENTION

The invention involves an orthopedic fixation system for fixing a bone to an element which is a bone fragment or a prosthesis. The system includes a length of flexible, inelastic cord, a first fastener for attaching the cord to the element; and a second fastener for fastening the cord to the bone. At least one of the fasteners has an opening through which the cord may pass from the interior of the bone to the exterior to enable the element to be securely mounted to the bone.

In one embodiment, the invention involves a fracture relief system in which bone fragments are brought together by internal, inelastic flexible cords to counter forces tending to widen the fracture interfaces when the bone is stressed through normal, though often restricted, physical activity of a patient. Movement of fracture surfaces away from each other thus is prevented, but the flexible, inelastic cords do not restrict the transfer of compressive stress from one fragment to another across fracture interfaces during physical activity. That is, the cords do not prevent the bone fragments forming a fracture interface from converging slightly to enable stress transfer. Due to their inelastic nature, the flexible cords do not maintain the fracture interface in compression during rest, and thus resorption of bone due to excessive constant compressive force is largely avoided.

In another embodiment, the invention relates to a bone fracture reduction system for positioning bone fragments with respect to each other to reduce a fracture and promote healing. The system comprises a flexible, inelastic cord having an end portion, a fastener attached to the end portion of the cord and adapted for attachment to a bone fragment in a direction generally coaxial to the axis of the end portion, and a second fastener attachable to the other bone fragment and having an opening through which the cord can be drawn to place the cord in tension. The second fastener includes a lock for locking the cord to the second fastener to restrain separation of the bone fragments.

In a further embodiment, the invention provides a bone fracture reduction system for reducing and promoting healing of a bone fracture. The fracture reduction system comprises a fractured bone normally having an exterior cortical portion and a non-cortical interior, the bone having bone fragments with confronting fracture surfaces. An internal fastener is attached from within the bone interior to a first bone fragment with a length of flexible, inelastic cord extending within the bone interior and attached to said fastener and passing outwardly through an opening in a second bone fragment. The fastener and cord are so positioned as to draw respective fracture surfaces together to reduce the fracture upon tensioning of the cord extending outwardly through said opening. A second, external fastener desirably is attached to the bone opening, this fastener including an open bore to receive the cord and a lock to secure the cord to this fastener.

The invention also relates to a method for positioning fragments of a bone fracture with respect to each other to reduce the fracture and promote healing of a bone which normally has an exterior cortical portion and a non-cortical interior, the bone fragments having confronting fracture surfaces forming a fracture interface. The method comprises attaching from within the interior of the bone to a first bone fragment an internal fastener to which is attached a length of flexible, inelastic cord, and drawing the cord through an opening formed in a second bone fragment to draw the fragments together in a direction to reduce the fracture. The cord preferably is secured to the second bone fragment to maintain the bone fragments in a predetermined position to transfer compressive loads through the fracture interface during physical activity. Desirably, the method includes the step of determining the direction of tensile force desired to draw the fracture surfaces together, and positioning the cord approximately parallel to that direction. A tensioning instrument may be provided, the instrument having a first end portion grasping the cord that protrudes outwardly from the second bone fragment and a second end portion in contact with the external fastener, the method including the step of operating the instrument so as to separate said end portions and thus place the cord in tension to draw the bone fragments into the desired position.

A plurality of internal fasteners may be fastened to different ones of a plurality of bone fragments, the internal fasteners having attached to them the length of flexible inelastic cord. The internal fasteners are so positioned with respect to each other that when the cord is tensioned, the bone fragments are drawn together in directions to properly join their respective fracture surfaces. As desired, one or more of the interior fasteners may include a pulley surface, such as that provided by an eyelet, over which the cord is movably trained to change the direction of the cord within the interior of the bone, the method including the step of pulling the cord over the pulley surface to tension the cord and properly position the bone fragments with respect to each other.

The flexible, inelastic cord system and methods of the invention may be employed to mount prosthetic devices to bone, such as acetabular cups to the acetabulum, bone plates to long bones, etc. Speaking broadly, a length of flexible, inelastic cord may be fastened at one end to a bone of a patient, the cord extending within the bone to a prosthesis which is to be held to the bone. For example, in the case of an acetabular cup, several cords may be employed that extend generally radially outwardly of the cup within the pelvis to maintain the acetabular cup in position.

BRIEF DESCRIPTION OF THE DRAWING

FIG. 1 is a partial cross sectional view of a fractured bone to which a cord fracture fixation device of the invention is being applied to reduce the fracture;

FIG. 2 is an exploded view, in partial cross section, of a device of the invention shown in FIG. 1;

FIG. 3 is a partially exploded view, in partial cross section, of the device shown in FIG. 2;

FIG. 4 is a partially exploded view, in partial cross section, of a modification of the device shown in FIG. 3;

FIG. 5 is a partially exploded view, in partial cross section, of another modification of the device shown in FIG. 3;

FIG. 9A is a broken away cross sectional view of an elbow olecranon fracture to which a fracture fixation device of the invention is being applied;

FIG. 9B is a broken-away, cross sectional view taken along line 9B—9B of FIG. 9A;

FIG. 10 is an end-on cross sectional view of a fractured bone to which a fracture fixation device of the invention has been applied;

FIG. 11A is a side view of a bone plate shown also in FIGS. 9A and B;

FIG. 11B is a top view of the plate of FIG. 11A;

FIG. 11C is a cross sectional view taken along line 11C—11C of FIG. 11B;

DESCRIPTION OF THE PREFERRED EMBODIMENTS

Figure 6A:
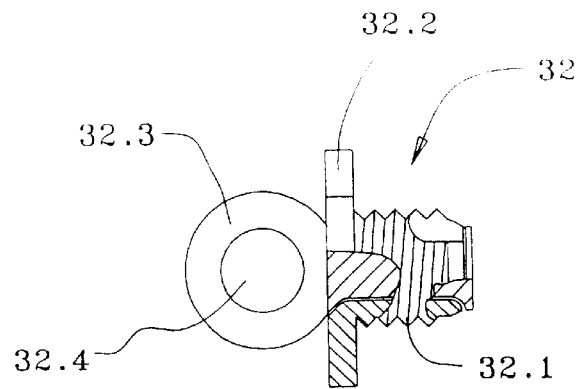
FIG. 6A is a view in partial cross section, of a fastener of the invention having a pulley surface.

As used herein, "cord" refers to any of a variety of materials that are strong in tension, inelastic, flexible, and biocompatible. If desired, the cord can be made of an organic suture material, or may be made from bioabsorbable materials such as poly (lactic acid). Preferably, however, the cord is made of a metal wire, preferably in the form of a metal wire braid for improved flexibility. Stainless steel is an appropriate and preferred material. The cords are sufficiently flexible so that they substantially straighten within the bone interior when placed under sufficient tension to draw bone fragments together, that is, under a tension of about 5 or more newtons. The cords may be made of a single material or composite, or may include sections of different materials chosen for their particular properties such as strength, flexibility, and radiopacity to enable the cords to be readily visualized by fluoroscopy.

The cords are sufficiently flexible as to exhibit substantially no axial compressive strength; that is, strength to resist axially applied compressive forces. The cords may be sufficiently stiff as to enable cord ends to be threaded through the eyelets of pulley-like fasteners and the like, but not sufficiently stiff to prevent bone fragments joined by a cord from converging, as is the case with, for example, bone screws or rigid pins such as Steinman pins.

The cords also are inelastic. "Inelastic", as used herein, means that when a cord is placed in sufficient tension to draw bone fragments together, i.e., under tensile forces ranging generally from about 5 to about 800 newtons, the cord stretches elastically only a very small amount if at all, so that the internal cord lengths extending from one bone fragment to another within a bone are under essentially no tension after the fragments have been properly anastomatized. Preferably, the cords demonstrate elastic recovery at body temperature of no more than about 10% upon release of a stretching force of 800 newtons.

As a result, the fracture interfaces are not stressed in compression by the cords when a patient is at rest, compression stress instead being applied intermittently through physical activity.

Referring first to FIG. 1, which illustrates a simple version of the invention, a fractured bone 10 is shown in schematic form as having a cortical portion 12 and an interior portion 14 that is non-cortical. "Cortical" bone refers to the hard, dense, outer shell of a bone that bears stress in normal physical activities. The interior or non-cortical portion of some bones may simply be hollow, or may have interconnected trebeculae of cancellous bone. The cortical shell portion of bones typically ranges in thickness from about 2 to about 10 mm. As shown in FIG. 1, the bone has been broken into two bone fragments 16, 18. The fracture surfaces of these bone fragments are shown at 16.1 and 18.1, respectively.

In the cortical bone portion 12 of fragment 18, there is placed a screw-type internal fastener 20, the designation "internal" referring to the fact that the fastener is attached to the bone fragment 18 from within the non-cortical interior of the bone. A flexible cord 22 attached to the fastener 20 extends across the interior of the bone as shown. Another screw-type fastener 24 is attached to the cortical portion of the other bone fragment 16. Fastener 24 may be termed an "external" fastener because it is attached to the bone fragment 16 from the exterior of the bone rather than the interior. Fastener 24 has a hollow bore through which the cord 22 passes to the exterior of the bone. A hand-operated cord tensioning instrument 26, which bears against the fastener 24 and also which pulls the cord 22, is used to tension the cord. A commercially available instrument of this type, commonly known as a Hall tensioning instrument, is described in Hall, U.S. Pat. No. 4,050,464, the teachings of which are incorporated herein by reference.

Fasteners 20 and 24 are so positioned that when the cord between them is placed in tension, the fracture surfaces 16.1, 18.1 will be brought together at a fracture interface with the interface being maintained under compression as long as the cord 22 is maintained in tension. The external fastener 24 is provided with a locking device 28 in the form of a screw that is received in a threaded bore in the fastener 24 and which, in this embodiment, clenches the cord between the fastener and screw to hold it in place. The tensioning instrument 26 is operated until the cord 22 between the fasteners is straightened and the fracture surfaces of the fragments are properly joined. While moderate cord tension is maintained, the locking screw 28 is inserted in the fastener 24 to clamp the cord in place. Slight further movement of the fragments toward each other relieves the tension in the cords, and the cords thereafter serve to prevent separation of the fracture surfaces as a patient engages in normal (although likely initially restricted) physical activity while freely permitting stress transfer across the fracture interfaces. Inasmuch as the newly formed bone at the fracture interface is subjected to stresses normally borne by that bone, the resulting collagen fiber matrix having the correct alignment and providing a strong union between bone fragments.

It is of importance to properly locate the fasteners 20, 24 so that the resulting direction of the cord 22 is such as to reduce the fracture and maintain the bone fragments in the proper position for healing. A variety of devices and instruments may be employed to properly place the fasteners. Internal fastener 20 can generally be placed where needed because the fracture site itself is open and accessible to the surgeon.

The procedure associated with FIG. 1 involves the steps of gaining access from the interior of the bone to the desired position for the fastener 20, drilling a small pilot hole through the cortical bone at this location from the bone interior, providing the fastener 20 with cord attached, and threading the fastener into the pilot hole, the fastener cutting its own threads. If the site for the fastener 20 cannot be readily accessed, an access hole can be drilled into the opposite side of the bone across from the desired site and the site may be accessed through this hole with the cord being drawn downwardly (in FIG. 1) through the hole formed for the external fastener 24. Although the fasteners 20, 24 in FIG. 1 and the fasteners described below are illustrated as having an elongated portion (threaded in FIG. 1) that extends approximately perpendicular to the surface of the bone, the fasteners may be attached at such other angles to the bone surface as may be appropriate to allow the force vector of the cord to parallel the axis of the fastener.

As described in greater detail below, one may employ a flexible, elongated tool to reach into the bone interior to properly place the fastener. A guide wire may first be placed in the bone interior with the tip of the wire adjacent the position of the desired internal fastener. The elongated tool may have a hollow interior to enable it to slide over the guide wire and into the proper position, following which the tool may be operated to perform the needed drilling and fastener replacement procedures. Fluoroscopy may be employed to aid the surgeon in this procedure.

The surgical procedures involved in the present invention are particularly beneficial for several reasons. First, through careful placement of the fasteners, the desired force vectors may be obtained to pull two or more bone fragments together and affect proper union of their respective fracture surfaces. Second, placement of the fasteners is a fairly simple technique and does not require substantial tissue division or removal of supportive tissue (i.e., muscle, tendon) from a bone.

Figure 7:
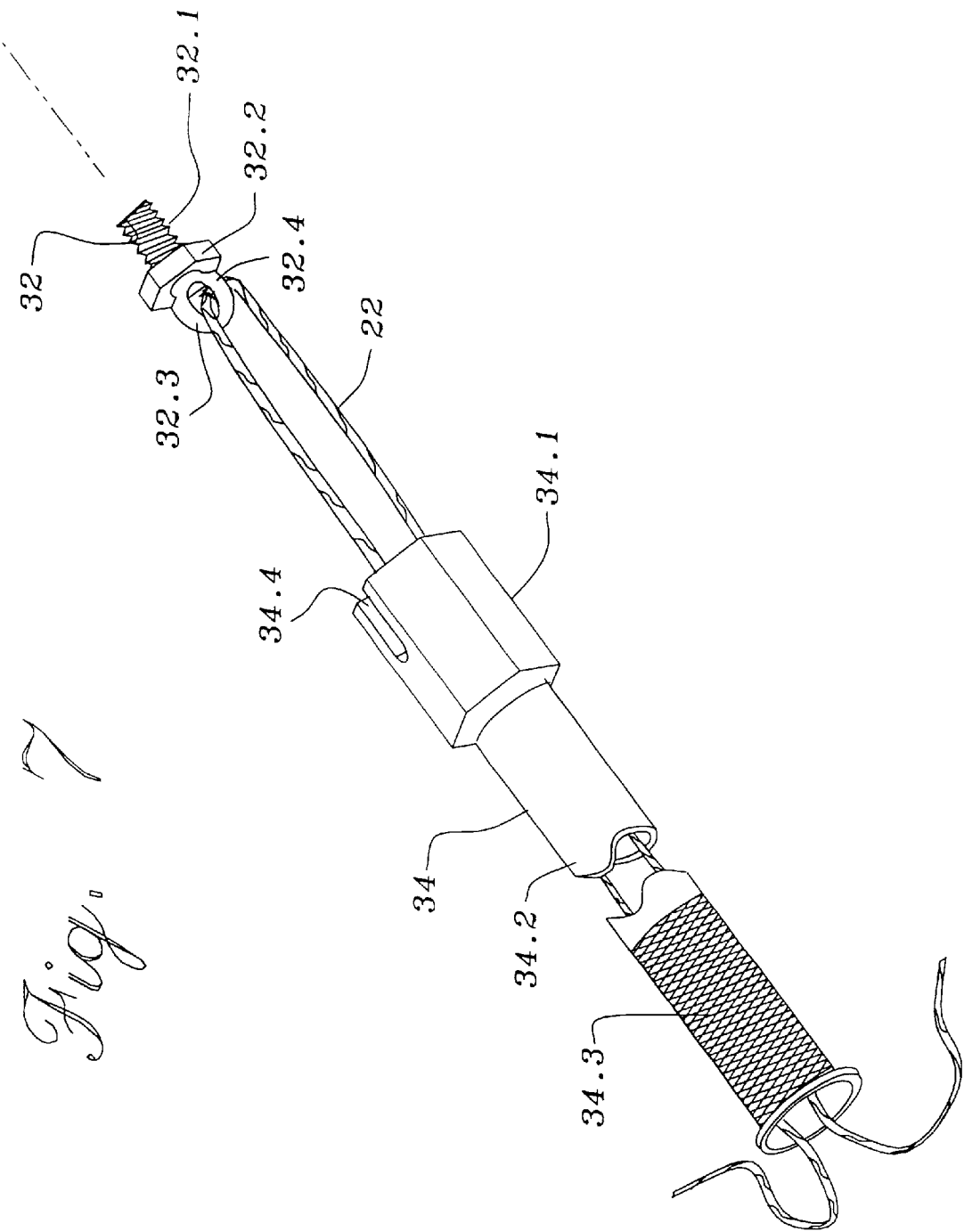
FIG. 7 is a perspective view, partially broken away, of a step in the installation of the pulley attachment element of FIG. 6A.

FIGS. 2 and 3 show the fastener and cord structure described above in connection with FIG. 1. The cord 22 may have an enlarged end portion 22.1 which may be a crimped-on sleeve, a welded-on collar, etc. The cord 22 is inserted in a hollow bore 20.1 formed through the fastener 20, the enlarged end 22.1 of the cord coming to rest within an enlarged distal end portion 20.2 of the bore. The proximal end 20.3 of the internal fastener 20 is provided with an appropriate shape, such as a hexagonal perimeter or recess, to enable it to be turned by an appropriate tool such as a hollow, flexible nut driver as shown in FIG. 7 or an Allen wrench, or by some other means.

Internal fastener 20 desirably has self-cutting threads 20.4 of a design commonly utilized for bone screws. The cord and the fasteners must be sufficiently strong, of course, to bear the expected tensile stress to be placed on the cord. The external fastener 24 in FIGS. 2 through 5 has similar thread-cutting threads 24.2, and a generally hexagonal head or other appropriate shaped proximal end 24.1 to receive a tool such as the nut-driver of FIG. 7, the tool preferably having a hollow interior through which may pass the cord 22.

As shown best in FIG. 2, the exterior fastener 24 has an interior bore 24.3 sized to slidingly receive the cord 22. At the proximal end of this fastener, the bore has a widened, proximally open portion with interior threads 24.4 sized to threadingly receive the threads 28.1 of a locking screw 28. The threaded bore 24.4 has one or more, preferably four, circumferentially spaced, axially extending slots 24.5 that are sufficiently wide to permit the cable to pass into them as shown in FIGS. 3–5. Locking screw 28 is formed with a rounded distally facing nose 28.2 configured to come into contact with the cord when the cord extends through the slot 24.5, as shown in FIG. 3, the cord being pinched between the nose 28.2 and the interior of the fastener 24 to lock the cord in place. In the event the cord must be re-tensioned to adjust the position of a bone fragment, the locking screw 28 can be backed out readily from the fastener 24, the cord re-tensioned as needed, and the locking screw 28 repositioned in the fastener.

Several different internal fasteners are shown in FIGS. 4 and 5. FIG. 4 illustrates a fastener 20.5 in the form of a toggle, the fastener having an elongated, axially slotted shank 20.6 carrying at its distal end a pair of elongated arms 20.8 capable of swinging from the folded position shown in dashed lines in FIG. 4 to the fully extended position shown in solid lines in FIG. 4, the arms being pivotally attached to the shank by a pivot pin 20.7. In use, the internal fastener 20.5 is passed from the interior of the bone through a hole formed in a bone fragment until the arms 20.8 clear the hole, following which the arms may move into the position shown in solid lines in FIG. 4 to contact the outer surface of the bone and thus anchor itself to the bone.

FIG. 4 also shows, as the exterior fastener, a dynamic compression plate 24.5 of known design, the plate having a ramped orifice 24.6. Within the orifice is received a complementary shaped insert 24.7 having an aperture 24.8 threaded to receive the locking screw 28. Cord 22 extends through the aperture 24.8, and the locking screw locks the cord to the insert.

Illustrated in FIG. 5 is an internal fastener 20.9 having a body carrying a pair of spring-loaded arms 30. Arms 30 are capable of being elastically pressed inwardly against the body 30.1 of the fastener to enable the fastener to be received through a bore formed in a bone fragment, the arms 30 springing outwardly into contact with the walls of the bore to anchor the fastener in place. Various other fasteners of the types used to anchor sutures, such as the well known "fishhook" types, may be used.

As described in greater detail below, the internal fastener may have an internally extending eyelet or ring to provide a pulley-like surface over which the cord may be trained. With reference particularly to FIGS. 6A and 7, fastener 32 is provided with a body 32.1 having self-tapping threads adapted to screw into cortical bone (into which is first preferably drilled a small pilot hole) and a hexagonal head 32.2. The fastener includes a swivel body 32.3 that carries an eyelet 32.4 and that is attached to the threaded body 32.1 by means of a swivel mounting shown best in FIG. 6A. As illustrated, the threaded body 32.1 may have a hollow interior within which is rotatably mounted the swivel body with the latter having a flared end engaging the threaded body and preventing the swivel body from escaping.

Referring now to FIG. 7, a tool for mounting the threaded internal fasteners of the invention is shown generally at 34. The tool includes a distal end 34.1 having a hexagonally shaped recess to encounter the hexagonally shaped head portion of the fasteners, but Allen wrench configurations (in which the tool has a solid hexagonal end portion and the fastener head has a hexagonal recess) and various other tool/fastener shape configurations may be used as well. The tool includes an elongated body portion 34.2 and handle portion 34.3 which may be conveniently knurled, as shown. Desirably, the tool is hollow so that a cord 22 can pass entirely through the tool, through the eyelet 32.4 of the fastener 32, and back through the handle of the tool. In this fashion, when the tool is rotated about its axis to thread the threaded body 32.1 into cortical bone, the proximally extending eyelet 32.4 may remain substantially rotationally stationary to avoid twisting the cord. If desired, the distally open end 34.1 of the tool may have an axially extending, distally open slot such as that shown at 34.4 through which the cord 22 may extend when fasteners of the type shown in FIGS. 1–3 are threaded into bone. As mentioned above, the hollow interior of the tool may be employed to follow over a previously placed guide wire.

Figure 8:
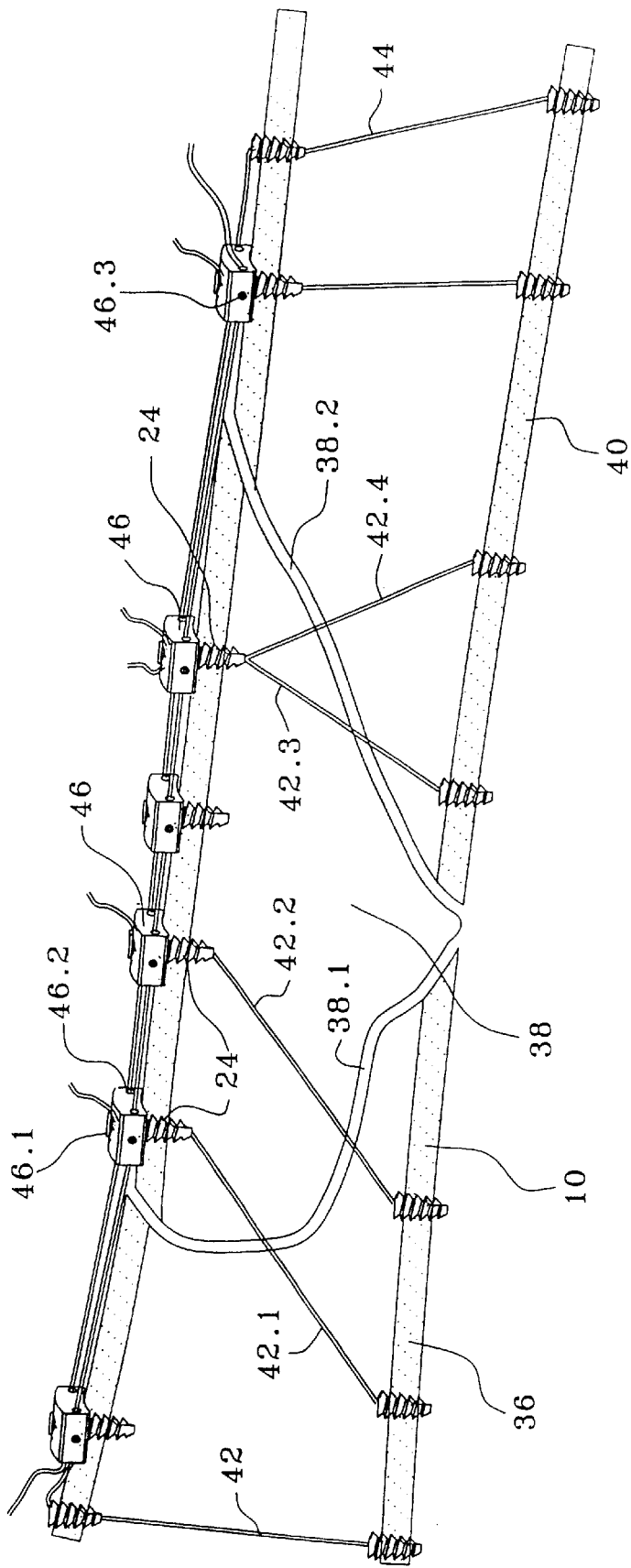
FIG. 8 is a partial cross sectional view of a fractured bone to which several cord fracture fixation devices are being applied to reduce the fracture.

FIGS. 8–10 illustrate various ways in which the devices of the invention may be employed. Referring first to FIG. 8, an elongated bone 10 is shown as having been broken into three bone fragments 36, 38 and 40. Cord systems of the type shown in FIGS. 1–3 are mounted at solid, unbroken end portions of the bones, the cords being shown as 42 and 44. A series of small bone plates 46, each having a curved bottom surface to fit against the exterior of the bone, are provided. Each of the bone plates has a central bore 46.1 for receiving an external fastener 24 and has one or more bores 46.2 extending within the bone plate generally parallel to the axis of the bone and capable of slidably receiving the cords 42, 44. One fracture 38.1 is reduced through the use of the cords 42.1, 42.2, and the other fracture 38.2 is reduced through the use of cords 42.3 and 42.4. Note that the latter cords each have proximal ends passing through a single external fastener 24. The cords 42, 44 extend laterally through the bores 46.2 in the bone plates, the cords being appropriately manipulated to properly bring together the fracture surfaces of the bone fragments. Cords 42, 44 may be locked to the end-most bone plates and to such other plates as may be desired through use of such locking devices as are typified in FIGS. 11A–11C; that is, a threaded bore such as that designated as 56.7 in these figures may be formed in the bone plates of FIG. 8 at an angle to and intersecting the cord-receiving bores 46.2. A set screw 46.3 or the like may be threaded into the threaded bore to engage the cord and lock it to the plate.

FIGS. 9A and 9B show the reduction of an olecranon fracture of the type that might result from trauma to the ulna by a fall on the outstretched hand, i.e., by the severely tensioned triceps. It is important here to reduce the fracture by drawing the bone fragments together and maintaining the fragments in proper alignment during healing, the fracture interface resisting separation under the force of the triceps.

Figure 6B:
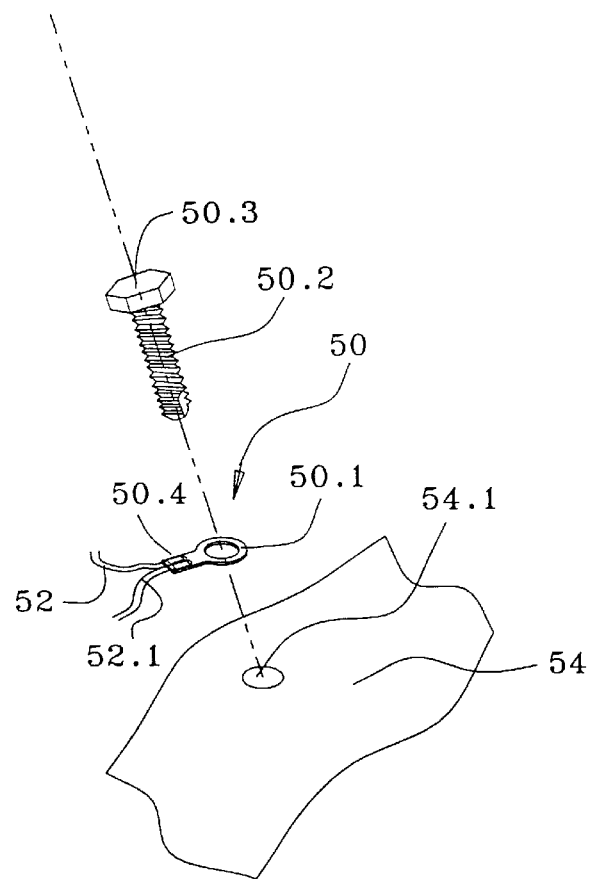
FIG. 6B is an exploded view of another fastener useful in the invention.

Here, an internal fastener 32 of the type shown in FIGS. 6A and 7 is placed from within the interior of the bone into the bone fragment 48, as shown in FIG. 9A. A second interior fastener 50 is placed distally from the fracture site within the ulna, as shown in the drawing, the vector between the fasteners 32, 50 denoting the direction of the resulting tensile forces that will be placed on the cord 52 extending between them. The fastener 50 may, if desired, include a pulley surface of the type provided by the eyelet 32.4 of the fastener 32 in FIG. 9A, or may be of a different design such as the type shown in FIG. 6B. The latter fastener comprises a ring 50.1 to be received against the surface of the bone 54, and a bone screw 50.2 having a ring-contacting wide head such as the hexagonal head shown at 50.3, the threaded portion of the screw 50.2 being sized to pass through the ring 50.1 and into a pilot hole 54.1 formed in the bone to securely fasten the fastener 50 to the bone. Cords 52, 52.1 are attached to the fastener by a crimp such as shown at 50.4 or by other means.

Fractures of such bones as the olecranon and the patella can result from extremely high tensile forces that are generated, in the case of the olecranon, by the triceps muscle, and, in the case of the patella, by the quadriceps muscle group. Reduction of fractures in these bones in the past has been accomplished through the use of external wires in what has become known as a "figure of eight" technique, the wires being trained around the ends of pins protruding from the bone fragments and the wires themselves laying against the outer bone surface. This external fixation technique has many of the drawbacks associated with cerclage techniques in that placement of the wires requires exposure of substantial exterior bone surface areas with associated loss of connective and supportive tissue. The use of extensive external wire structures can be largely avoided or eliminated in accordance with the present invention.

Referring again to FIG. 9A, the cord 52 extends from the fastener 50 through the eyelet 32.4 of the fastener 32 and thence out through an opening formed in the bone. If desired, the fastener 50 can be attached by utilizing screw fasteners having self-drilling and self-tapering screw portions, as shown in FIG. 7. An elongated tool having a right-angled drill adapter can be employed to attach the fastener to the bone. The cord 52.1 similarly is drawn out through the opening formed in the bone. An exterior fastener of the type described in connection with FIGS. 1–3 may be employed at the opening of the bone, the cords 52, 52.1 passing outwardly through the fastener. After suitable tension has been applied to the cords, the cords can be secured to the fastener in the manner described above. If desired, the external fastener may include a bone plate 56 as shown. Preferably, two generally parallel but transversely spaced cord systems are employed, as shown in FIG. 9B.

It will be understood that as the cord 52 is tensioned, the bone fragment 48 will be pulled to the right into contact with the ulna to reduce the fracture. Fastener 32 acts as a pulley; as the externally extending portion of cord 52 is pulled, some mechanical advantage is obtained to reduce the fracture. If desired, only the cord 52 need be employed in this procedure to reduce the fracture and to maintain the fracture interface in position. It will be observed that in this event, the cord will exert force on the bone plate 56 in the direction of the fastener 32, and to counteract this force, the cord 52.1 may be employed to provide a counteracting, substantially balancing force vector. It will be noted that the cords 52, 52.1 together are positioned to counter the force exerted by the triceps, shown as T in FIG. 9A.

The bone plate 56 shown in FIGS. 9A and 9B is also illustrated in greater detail in FIGS. 11A, 11B and 11C. The plate 56 may be made of plastic or steel or other biocompatable, rigid material, and includes a top 56.1, a bottom 56.2 which is slightly concave in order to fit more closely the convex surface of bone such as the ulna as shown in FIGS. 9A and 9B, identical side walls 56.3 and identical end walls 56.4 tapered so as to avoid trauma to overlying soft tissue. Cord-receiving bores 56.5, 56.6 are formed at an acute angle to the top and bottom walls 56.1, 56.2, as illustrated best in FIGS. 11A and 11C. These bores intersect intermediate the top and bottom walls, and threaded bores 56.7 are formed in the side walls 56.3 and extend toward each other so as to intersect the bores 56.5, 56.6 at their point of intersection. The threaded bores 56.7 are so oriented as to receive a set screw (not shown) which, when fully inserted, engages cords passing through the bores 56.5, 56.6 to lock them in place.

FIG. 10 further illustrates the use of pulley-like fasteners within a bone. This figure shows a bone end-on, the bone having been broken into three fragments 58, 60, 62. Internal fasteners of the type shown at 32 in FIGS. 6A and 7 are placed from the interior of the bone into each of bone fragments 60, 62 with the cord 64 extending through the pulley-like eyelets of these fasteners. Both ends of the cord are drawn out of the bone through an external fastener 24 of the type shown in FIGS. 1–3, the latter being carried by bone fragment 58. The internal fasteners 32 and the external fastener 24 are so positioned that when the ends of the cord that extend outwardly through the external fastener are placed in tension and are then secured to the fastener 24 through the locking screw 28, the fragments are urged together to properly reduce the fracture and to prevent the fracture surfaces from separating. It should be understood that the pulley surfaces of the fasteners 32 enable slight movement of the cord 64 as stress is applied to balance any tensile forces in the cords and thus avoid unwanted shifting of one bone fragment with respect to another due to unequal loading.

Note also in connection with FIG. 10 that the vector of the resultant force applied to each bone fragment is not parallel to the direction of the cords, but rather depends for each fragment upon the angle between the cord segments leading to that fragment and the tension in each cord segment. Assuming that the tension in each of the three cord segments fracture reduction occurs is approximately the same, the vector of the resultant force acting on each fastener approximately bisects the angle between the cord segments leading to that fastener, and knowledge of this relationship may aid the surgeon in proper placement of the fasteners.

Figure 12A:
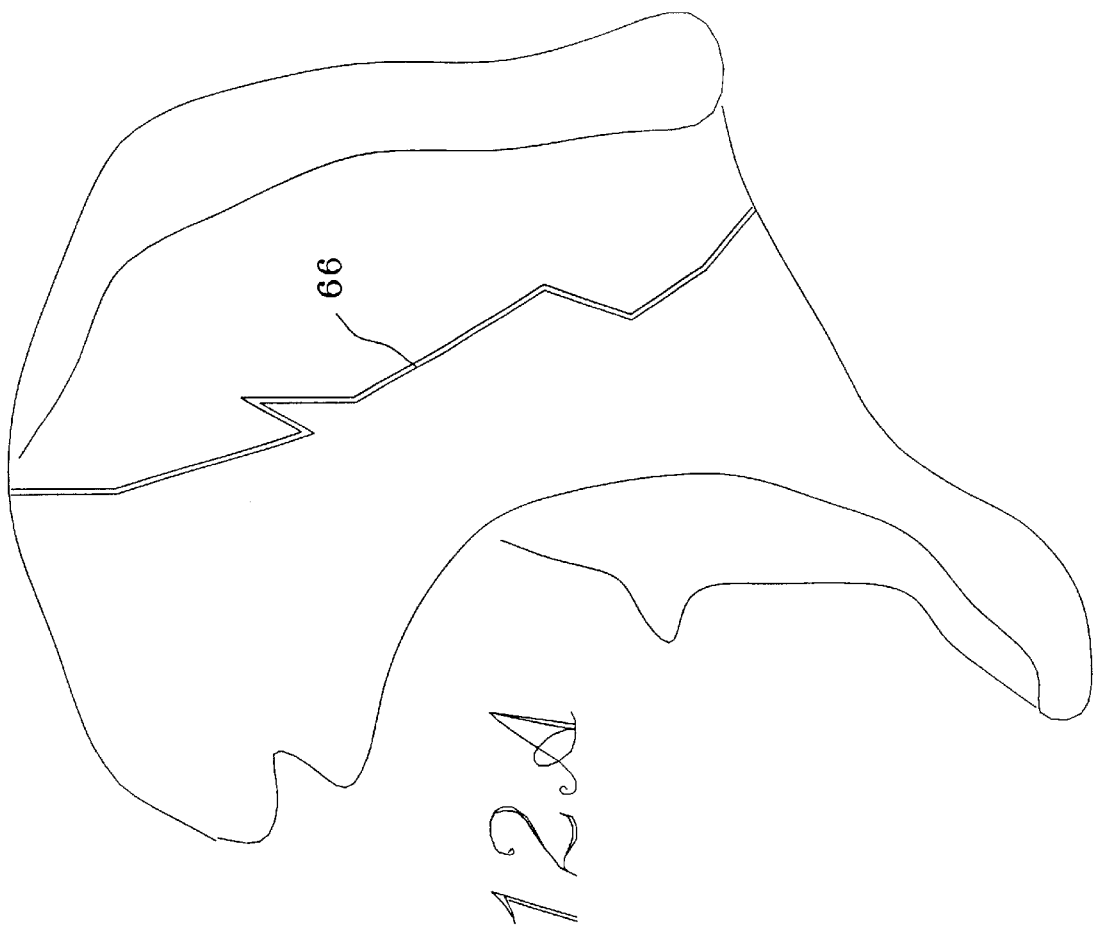
FIG. 12 A is a schematic representation of the pelvis, showing the location of a fracture in the ilium to be reduced by a method of the invention.
FIG. 12B is a cross sectional view of the pelvis of FIG. 12A showing a step in the reduction of the fracture.
FIG. 12C is a cross sectional view of the pelvis of 12A showing the reduced bone.
Figure 12B:
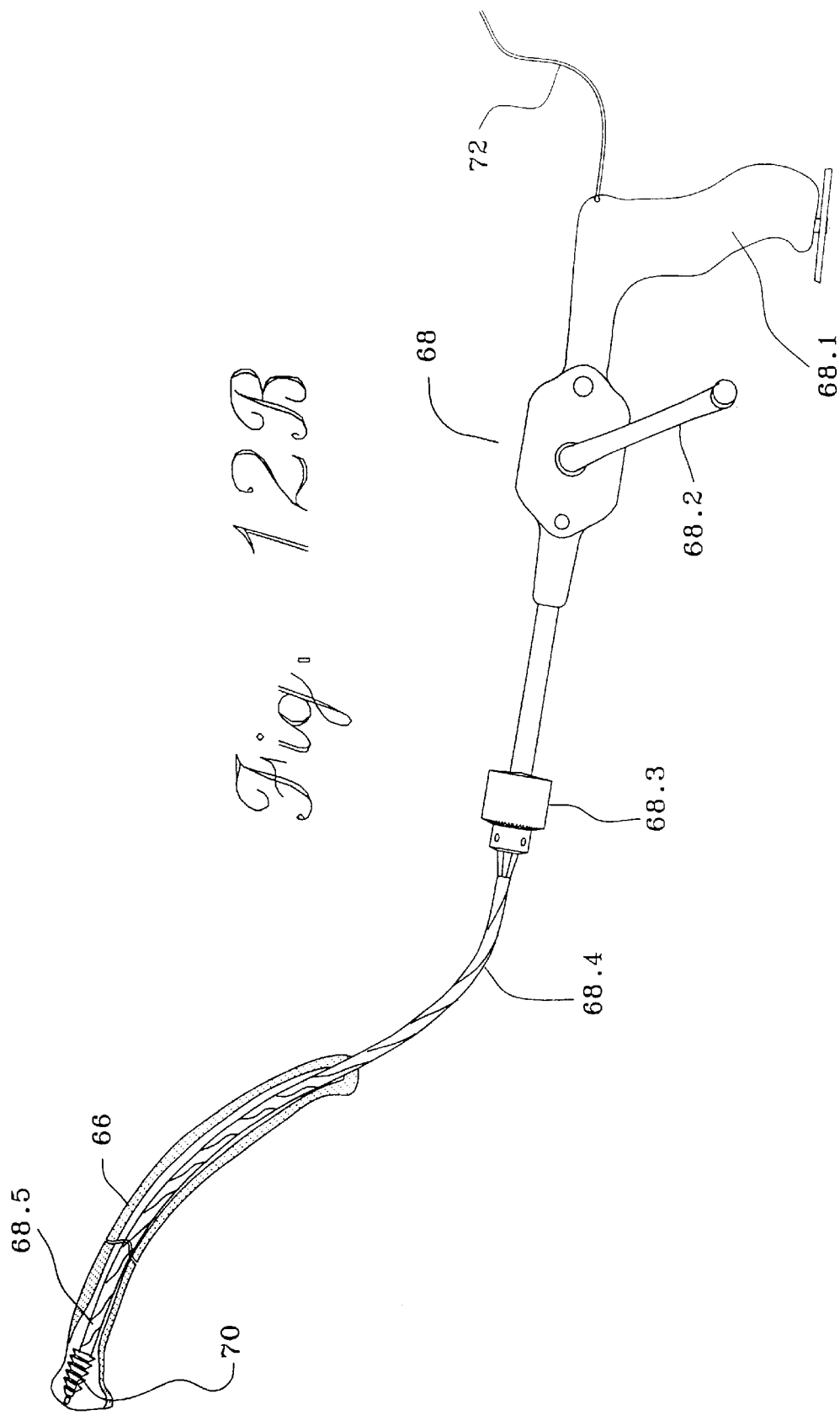
Figure 12E:
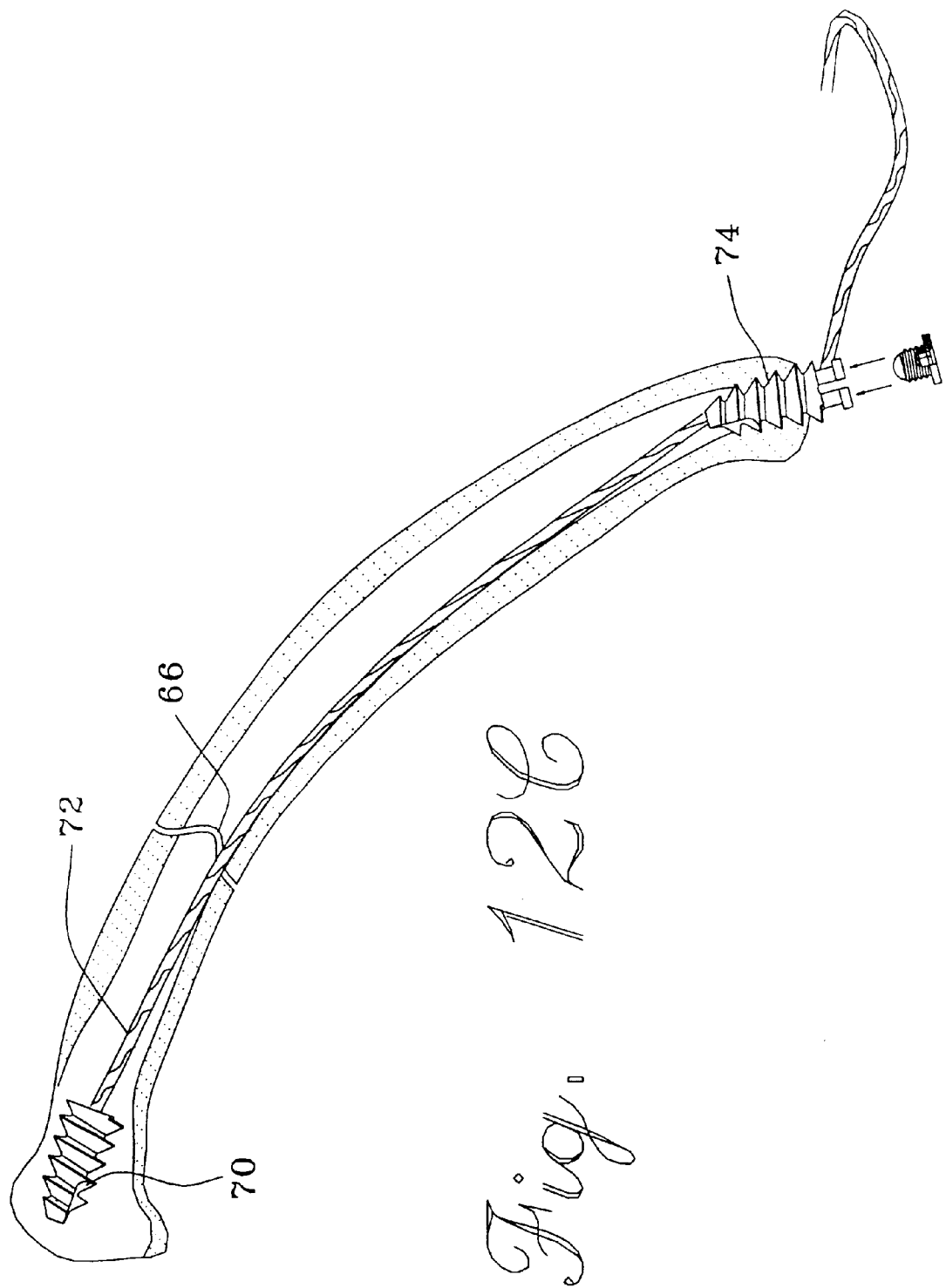

FIGS. 12A, 12B and 12C show steps in the reduction of a fracture of the ilium of the pelvis, the fracture being designated generally as 66. It is desired here to run a flexible, inelastic cord of the invention from within the pelvis to cortical bone on the far side of the fracture, fastening the cord to the cortical bone, the cord thus running past the fracture site and exiting the pelvis on the near side of the fracture site. Referring to FIG. 12B, installation of the cord and internal fastener is facilitated through the use of an external drill mechanism 68 as illustrated in this figure, and comprising a hand grip 68.1, a rotatable handle 68.2, a chuck 68.3, and a gear mechanism (not shown) that causes the chuck to rotate about its axis in response to turning of the handle 68.2. The drill may be of the type marketed by DePuy as its Modified Pease Bone Drill, Model 2079-00. A flexible cable 68.4 is provided, the cable being of known design and torsionally stiff so that rotation of the cable at its end where attached to the chuck 68.3 results in rotation of the cable at its distal end 68.5. An internal fastener of the type shown in FIG. 3 is shown at 70, and is provided with a hexagonal head which is inserted within a hexagonal end of the flexible cable 68.4 such that as the cable is rotated about its axis, the threaded fastener 70 is threaded into cortical bone with the cord (not shown) extending from the fastener through the hollow interior of the flexible cable 68.4 such that when the fastener 70 has been suitably fastened to cortical bone, the flexible cable can be withdrawn from the pelvis leaving behind it the flexible, inelastic cord within the bone.

The cord in FIG. 12C is designated 72, and extends from the internal fastener 70 across the fracture 66, around the bends in the ilium, and exits the pelvis through an external fastener of the type described above and designated 74. Although only one such cord is shown in the drawing, a plurality of such cords, extending in the necessary directions to reduce the fracture, may be employed. The cord 72 is placed under tension to reduce the fracture, and then is secured in the external fastener 74 in the manner described above to prevent the fracture interface from reopening.

Figure 13A:
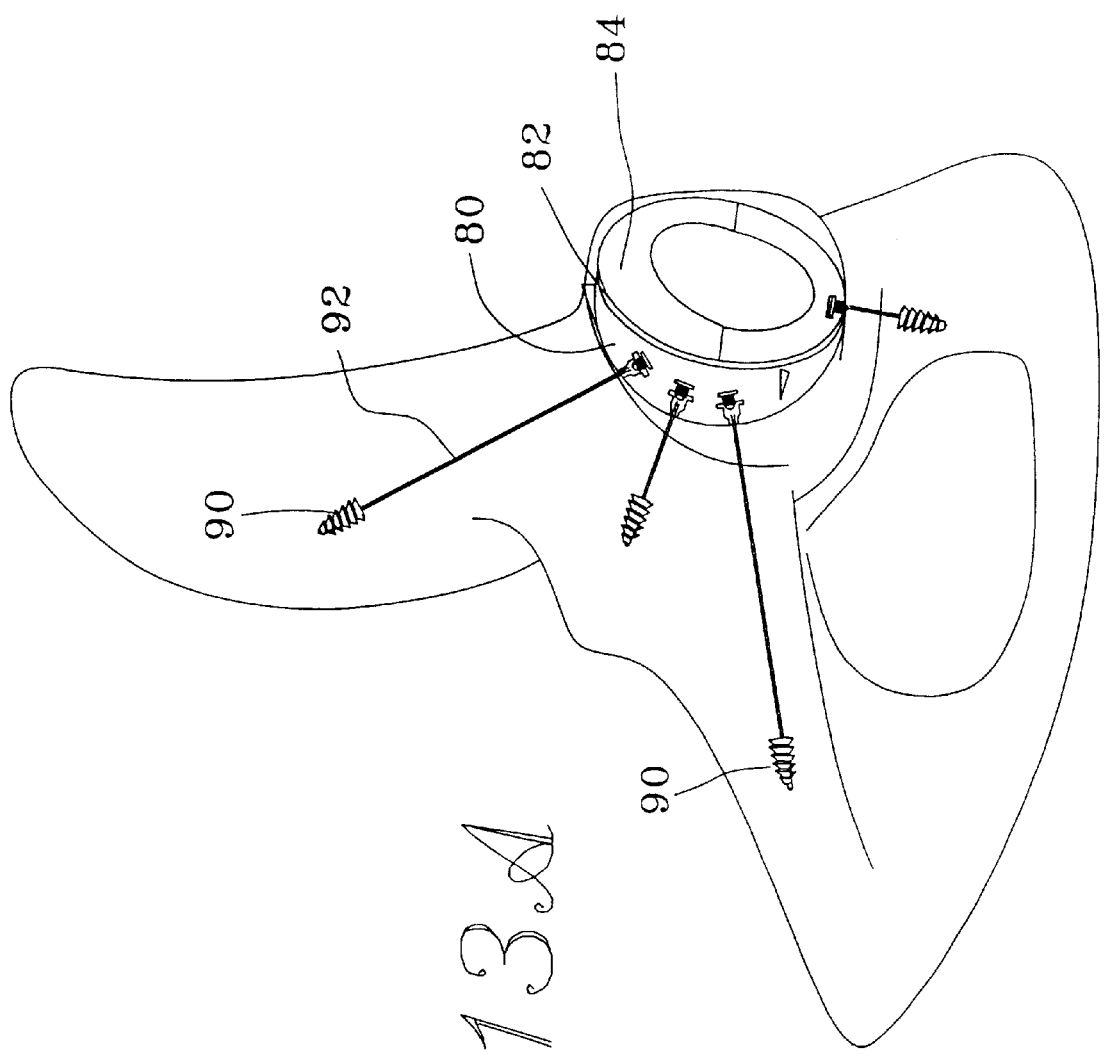
FIG. 13A is a schematic perspective view of a portion of the pelvis showing an acetabular cup prosthesis held in position by a cord system of the invention.
Figure 13B:
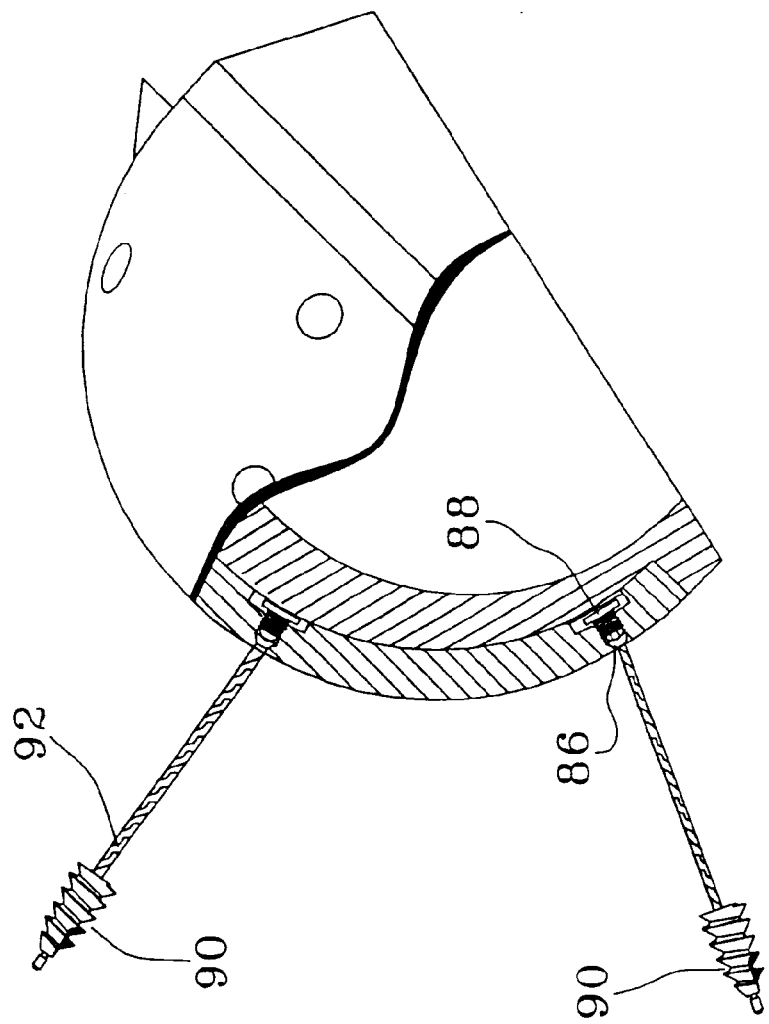
FIG. 13B is a partially broken away side view of the prosthesis shown in FIG. 13A.

FIG. 13A shows use of the cord system of the invention for fixation of a prosthetic acetabular cup to the acetabulum of a patient. Designated 80 in FIG. 13A is a prosthetic acetabular cup, commonly comprising a cup-shaped metal jacket 82 formed of titanium or other biocompatible metal, and an inner cup 84 having a generally hemispherical cavity in it to receive the ball of the femur. The outer surface of the metal jacket 82 may have threads or spikes or other surface configurations enabling it to grip tightly to the bony acetabulum once the latter has been surgically shaped to receive the prosthesis. In accordance with the invention, the generally cup-shaped metal jacket 82 is provided with a series of apertures 86 (FIG. 13B) which may be threaded to receive lock nuts 88, the threaded apertures and lock nuts themselves forming an external fastener as generally referred to above. Internal fasteners 90 are attached from within the pelvic bone to the cortical bone thereof in the manner described above in connection with FIGS. 12B and 12C, the flexible, inelastic cords 92 extending within the pelvis back through the apertures 86 in the acetabular cup prosthesis. Desirably, 3 or 4, or more, such cords are employed, extending preferably generally radially outwardly from the cup in a variety of different directions. The ends of the cords are individually suitably tensioned to properly position the acetabular cup prosthesis 80, the ends of the cords extending into the jacket then being locked in place through the use of the locking screws 88. The polymeric inner cup 84 is then placed in the jacket. The purpose of the flexible, inelastic cords 92 is to hold the acetabular prosthesis in place and, as needed, to repair fractures in the pelvis as well.

Referring now to FIGS. 14A–D, these figures depict how the flexible, inelastic cords of the invention may be used to reduce fracture of a long bone such as the humerus. A fractured humerus is designated 96 and includes a medullary canal 98 bounded by cortical bone 100. The fracture site is shown best in FIGS. 14D and 14F, the fracture interface being designated 102. At its distal end, on either side of the olecranon, the humerus has thin walled portions through which are drilled holes 104, 106 for introduction of a cord system of the invention.

Figure 14A:
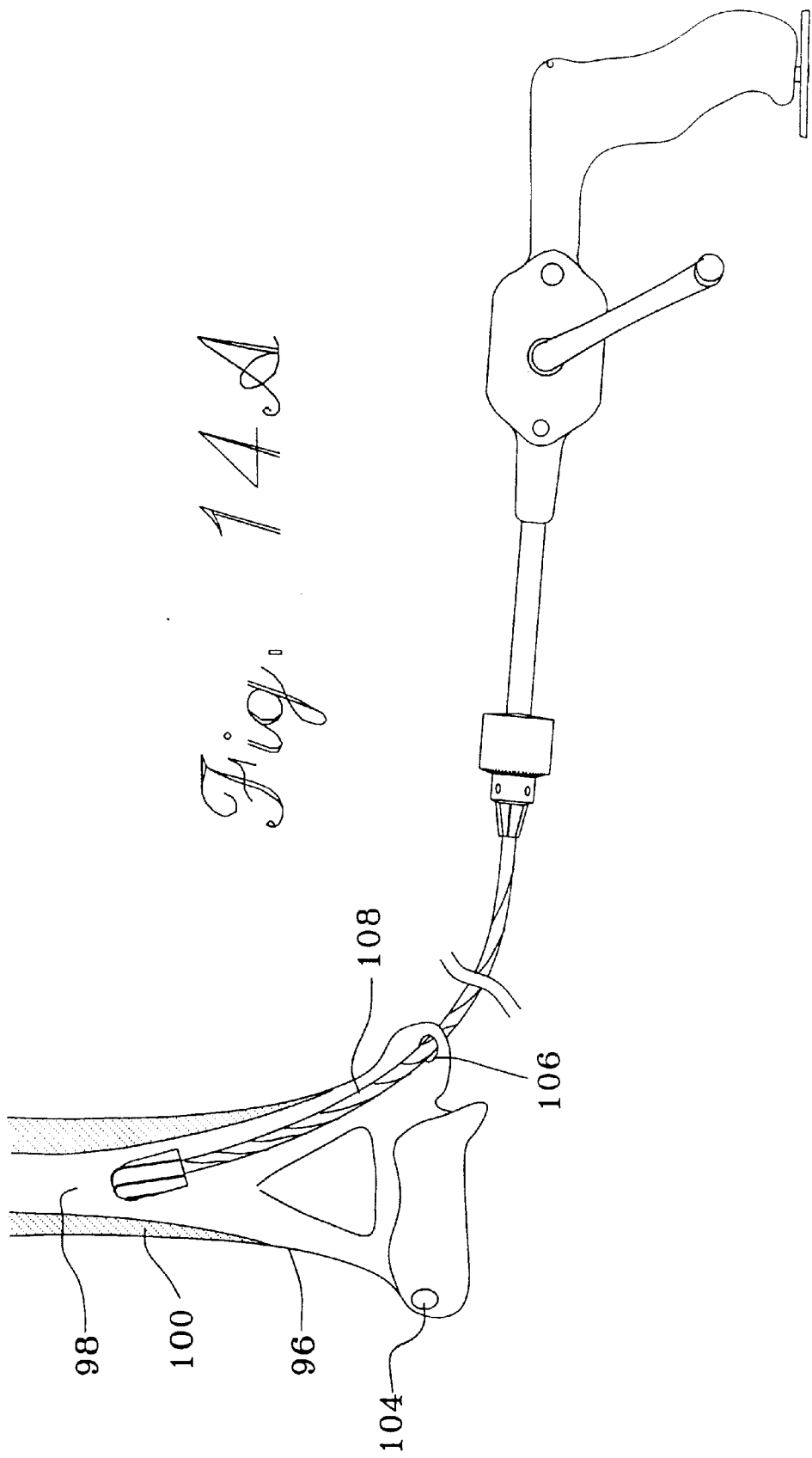
FIGS. 14A, B and C are schematic representations of the distal end portion of the humerus showing different steps in the placement of a cord system of the invention.
Figure 14B:
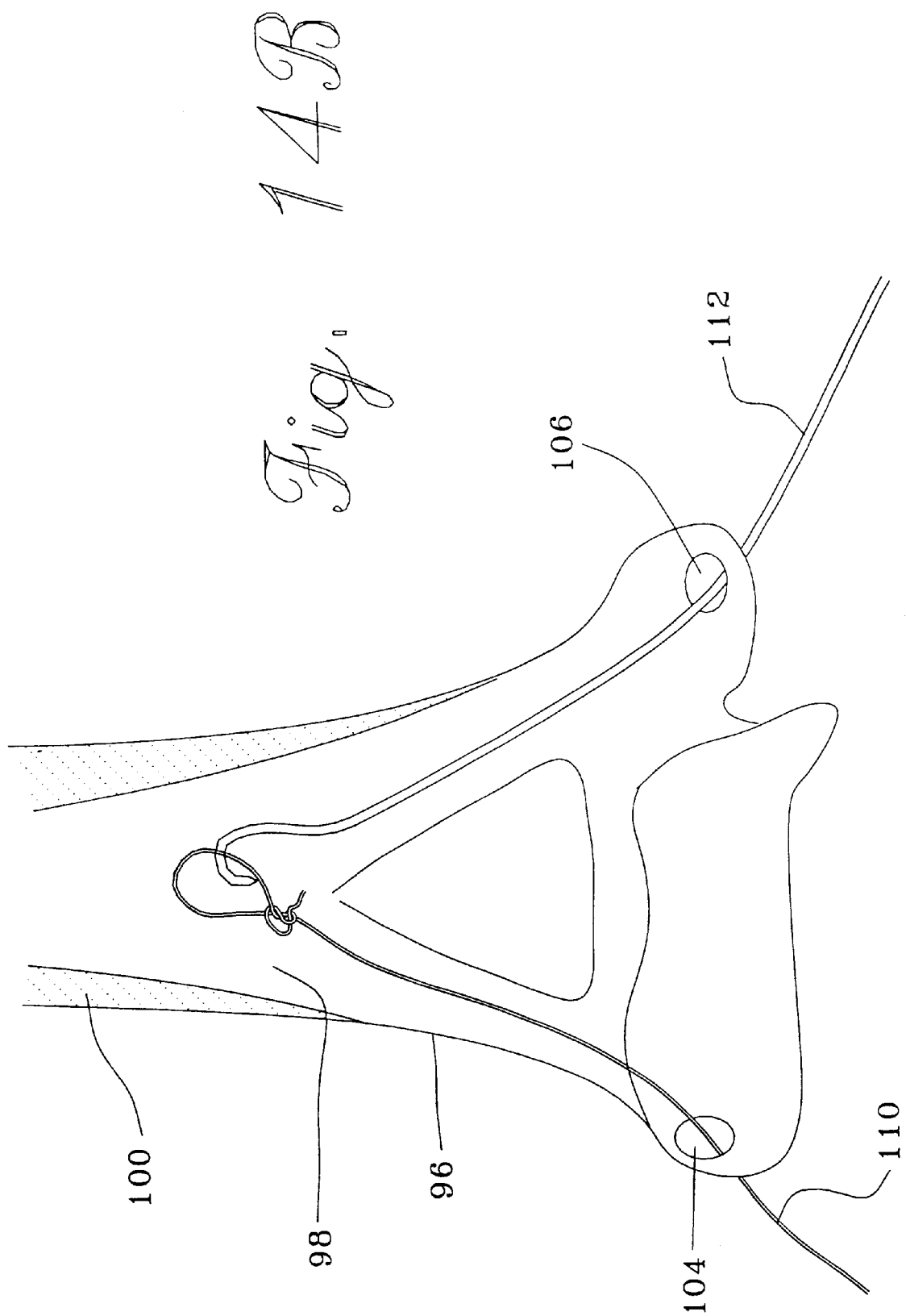
FIG. 14D shows a toggle type cord fixation system employed in the humerus mounted on a flexible installation rod and shown during insertion of the toggle.
FIG. 14E is a perspective view of a toggle of the type shown also in FIG. 14D.
FIG. 14F is a schematic view, in partial cross section, of the humerus showing a fracture relieved through the use of the toggle and cords shown in FIGS. 14A–14E.
Figure 14C:
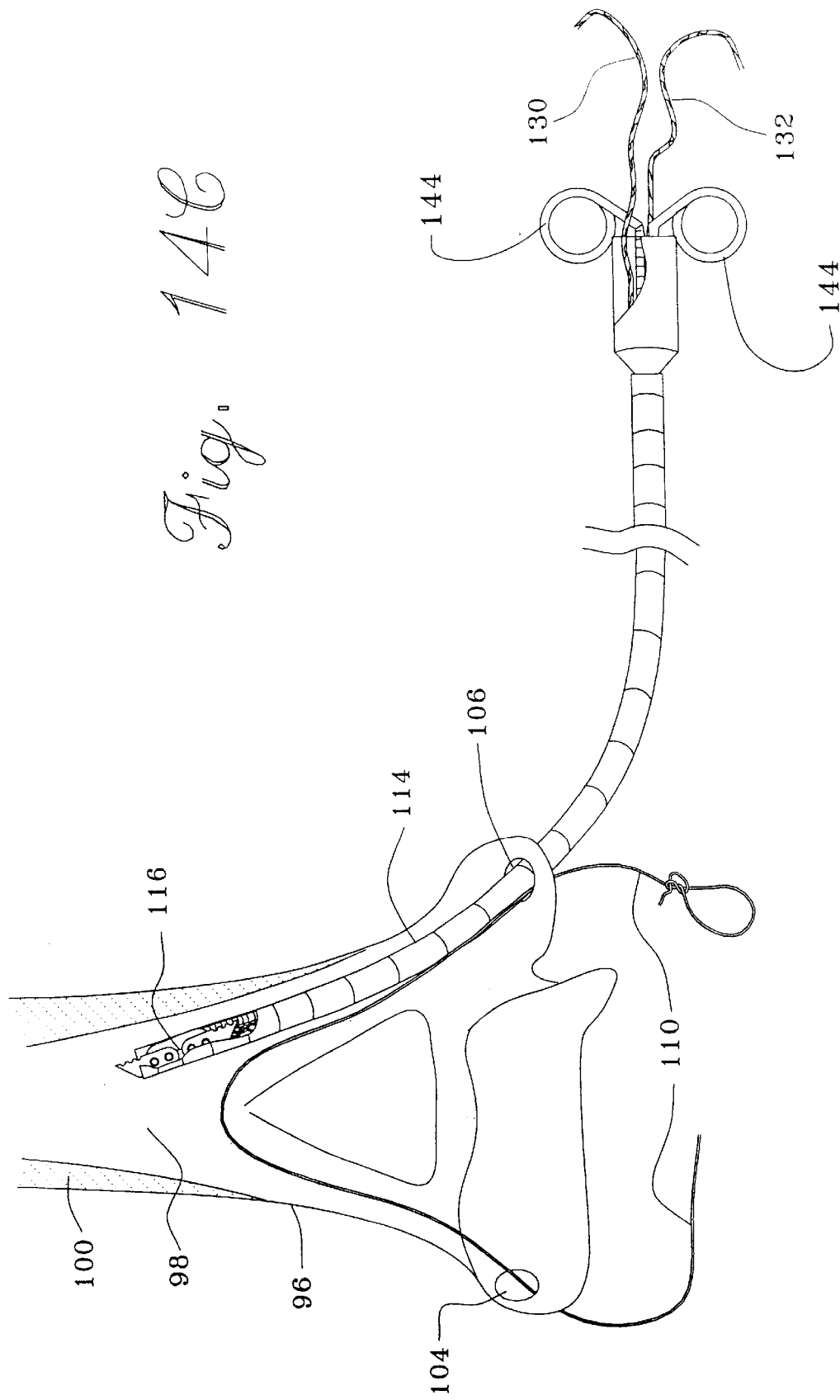

The holes 104, 106 may be formed through the use of a drill of the type described above, the drill having a flexible shaft shown schematically as 108 in FIG. 14A. The elongated bores formed by the drill 108 converge at a point spaced proximally from the olecranon, and further movement of the flexible drill shaft upwardly (proximally) within the medullary canal 98 serves to remove some of the tissue in the canal to make way for the cord system. It is desired, once the cord system is in place, that a pair of spaced cords traverse the fracture site within the medullary canal, each cord exiting at one of the holes 104, 106. For ease in placement of the cord system, each of the cords may initially exit through hole 106, with one of the cords thereafter being drawn downwardly through hole 104. This may be accomplished as shown in FIGS. 14B and 14C. A wire 110 having a loop at one end is inserted through the hole 104, the loop then being snared by a hook-shaped end of a snare wire 112 that is inserted through the other hole 106. The snare wire then can be removed and discarded.

Through the hole 106 is introduced a flexible, hollow introducer tube 114 carrying within it a toggle 116, the toggle being of the type shown best in FIGS. 14C through 14F. Turning to these figures, the toggle is shown as having an extended orientation in which it is received in the tube 114 (FIG. 14C) and in which it is eventually deployed in the medullary canal (FIG. 14F), and an articulated orientation (FIG. 14F) permitting it to be moved within the close confines of the medullary canal during placement of the toggle.

Referring to FIG. 14E, the toggle mechanism typified in the drawing has a body formed of a pair of parallel, spaced, elongated body strips 118 joined at their ends by transverse pins 120. Two pairs of parallel gripping arms 122 are provided, the arms of each pair being spaced and joined at their ends by a rod 124, and it is to these rods extending between the arms 122 of each pair that the ends of the cords 130, 132 are respectively attached through the use of eyelet connectors 126. The pins 120 that join the body strips 118 also pass outwardly through holes formed in the gripping arms intermediate their ends so that the gripping arms can pivot about the pins between extended and articulated orientations. Each gripping arm has an end 128 opposite the ends joined by the rods 124 that is serrated or otherwise configured for gripping to bone.

Figure 14D:
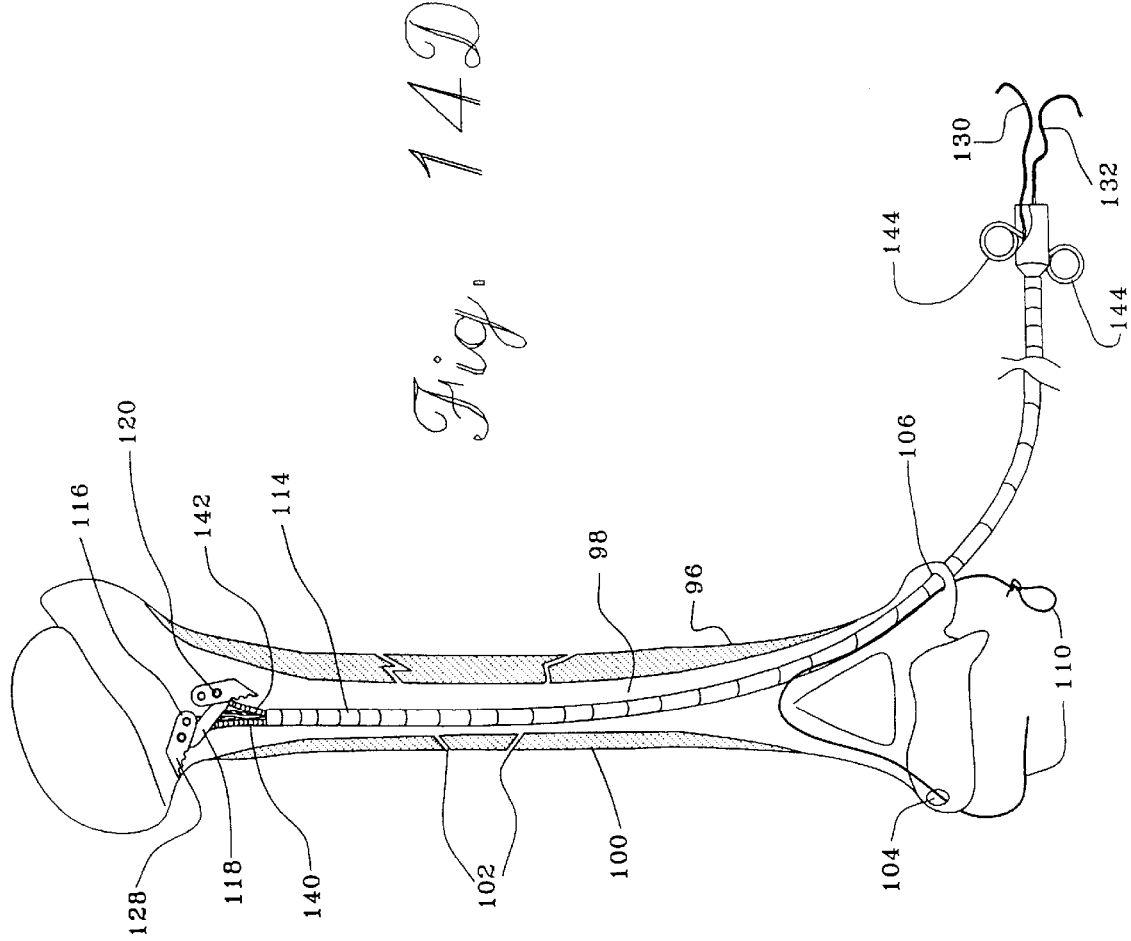

To properly position the toggle, a pair of flexible push rods 140, 142 are provided within the introducer tube 114, each push rod extending outwardly of the introducer tube as shown in FIG. 14D and being attached to manually graspable rings 144 that permit the push rods to move axially and also rotationally. The push rods may have transverse grooves, as shown at 146 in FIG. 14E, adjacent their ends, the grooves being sized to receive the transverse pins 120. The grooves may be disengaged from the pins 120 simply by rotating the push rods through 90 degrees. One thus may position the toggle as desired within the medullary canal through relative axial movement of the push rods 140, 142, and once the body of the toggle is in its desired location, the push rods may be rotated to disengage them from the toggle so that they can be removed. Moreover, once the body of the toggle has been oriented as desired, and optionally before removal of the push rods, tension is placed on the cords 130, 132, causing the arms 122 to pivot in the direction of the arrow A in FIG. 14E to cause the ends 128 of the arms to extend outwardly of the toggle body as shown best in FIG. 14F into gripping contact with bone on each side of the medullary canal.

Returning now to FIG. 14C, the flexible introducer tube 114, including within it the toggle 116 to which are connected the pair of flexible cords 130, 132, is pushed upwardly through the medullary canal to a point at which anchoring of the cords is desired, this, in FIG. 14D, being near the head of the humerus where the medullary canal becomes wider. The toggle 116 is then held in place within the medullary canal by the push rods 140, 142 attached to the transverse pins 120 of the toggle body, and the flexible tube 114 is then withdrawn slightly to expose the toggle within the medullary canal. By appropriate axial movement of the push rods, the toggle arms ends 128 are deployed outwardly into contact with the bone. Once approximate deployment of the toggle has been accomplished, the flexible tube 114 may be removed distally through the hole 106. Further manipulation of the push rods with respect to each other and to the bone may be required to achieve proper orientation of the toggle within the medullary canal. A 90 degree twist of each push rod frees it from the toggle and enables the push rods to be individually removed from the medullary canal. Of course, in this and other procedures described herein, fluoroscopy is used to insure proper placement of elements of the cord system.

At this point, it will be noted that both of the flexible, inelastic cords 130, 132 exit from the hole 106. The wire 110 with formed loop is now attached to one of the cords, cord 130 in this example, and pulling the wire 110 from the hole 104 draws the fastened cord 130 outwardly through the hole 104.

Figure 14F:
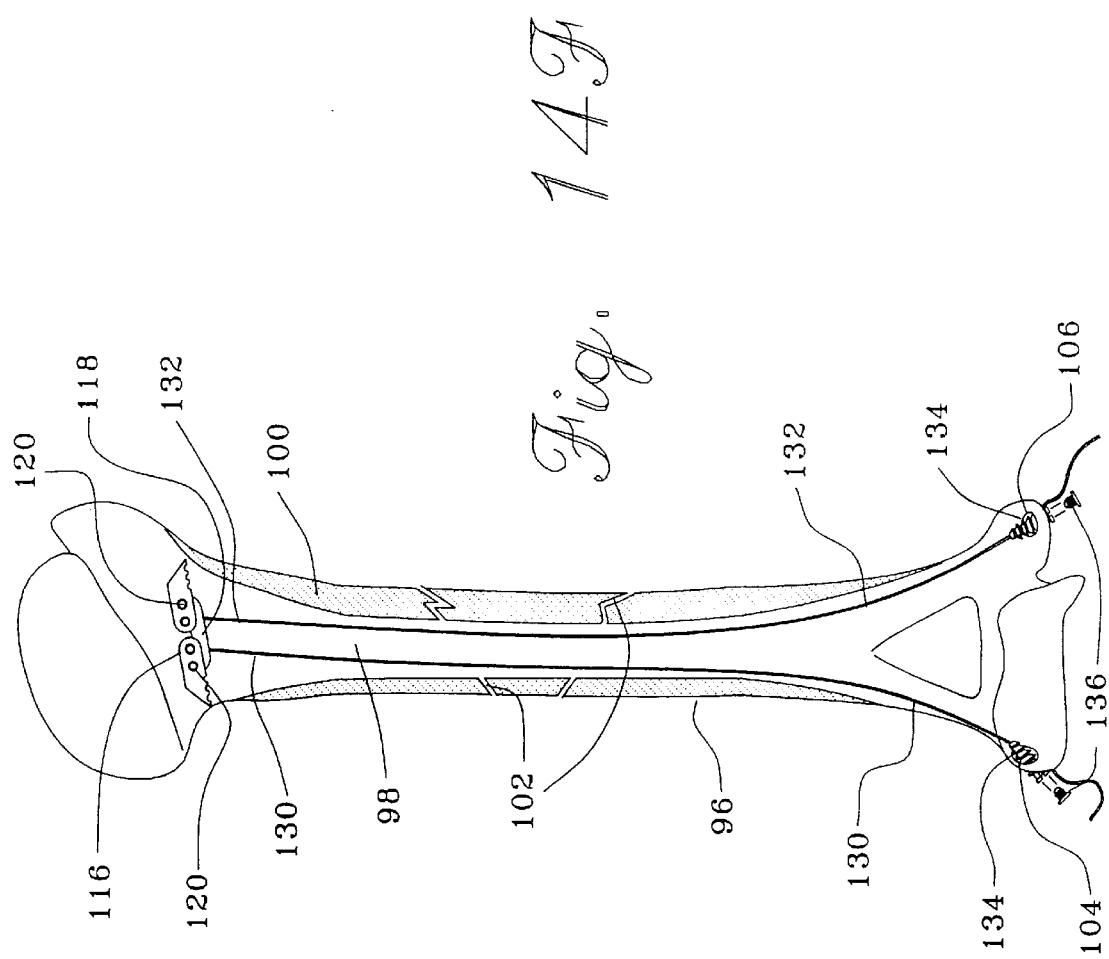

FIG. 14F shows the flexible, inelastic cord system in place in the humerus, the toggle device 116 being firmly anchored near the head of the humerus, the flexible, inelastic cords 130, 132 extending in a spaced orientation downwardly through the medullary canal with cord 130 exiting from the medullary canal through the hole 104 and cord 132 exiting from the other hole 106. External fasteners of the type described above in connection with FIG. 2 and designated 134 are screwed into the holes 104, 106 with the cords extending through these fasteners. By suitably pulling on the cords 130, 132 from the distal end of the humerus, one may bring together the fracture surfaces as desired. By spacing the cords from one another, the possibility of placing one side of the bone in tension and the other in compression is largely avoided. Once the bones have been appropriate located, the locking screws 136 are screwed into the ends of the fasteners 134, locking the cords in place. Because the cords are inelastic, any tension remaining in the cords after attachment of the locking screws 136 is quickly lost.

The invention is particularly adapted for use in situations in which a bone has been fractured into a number of fragments that need to be carefully brought back into alignment, with compression being generated at the fracture interfaces during physical activity to promote fracture healing. The use of external splints, casts, bandages, cerclage elements, and the like to reduce fractures in badly fractured bones is quite difficult. Exterior pressure must be used to force bones into the correct position and continued adequate compression of all or most of the fracture interfaces is difficult to attain. Through the use of the invention, in which fasteners are placed into bone fragments from the interior of the bone, with flexible cords being employed within the bone, to pull, rather than push, the fragments into place, the force vectors needed for proper fracture reduction and interface compression can be readily chosen at the time of surgery. When many bone fragments are involved, a surgeon may find it desirable to lead two, three or more cords out of the opening formed in one fragment with the interior ends of the cords attached to the variety of fragments via internal fasteners, the surgeon then operating the cords independently of each other to move the bone fragments into the desired position using fluoroscopy as needed to visualize the cords and proper placement of the bone fragments. The use of a cord having a degree of radiopacity aids visualization of the cord.

While a preferred embodiment of the present invention has been described, it should be understood that various changes, adaptations and modifications may be made therein without departing from the spirit of the invention and the scope of the appended claims.

We claim:

1. An orthopedic fixation system for fixing a bone having an exterior cortical portion and a non-cortical interior to an element which is a prosthesis or a bone fragment, comprising a length of inelastic, flexible cord; a first fastener for attaching the cord to said element, a second fastener for attaching the cord to the bone and enabling the cord to extend from said first fastener within the non-cortical interior of the bone to the second fastener, and a third internal fastener fastenable to bone from the interior of the bone and having a surface over which said cord may be movably trained to change the direction of said cord between the first and second fasteners.

2. A bone fracture reduction system for reducing and promoting healing of a bone fracture of a bone normally having an exterior cortical portion and a non-cortical interior and having bone fragments with generally confronting fracture surfaces, comprising an internal fastener attachable from within the non-cortical interior to a first bone fragment, a second fastener attachable to a second bone fragment, a length of flexible, inelastic cord having substantially no axial compressive strength and extendable within said bone interior and attached to said internal fastener and second fastener, and a third fastener fastenable from the interior of said bone to a third bone fragment and having a pulley surface interior of said bone over which said cord is movably trained to enable the direction of said cord within the interior of said bone to be changed.

3. Method for reducing a bone fracture in a bone having a cortical exterior portion and a non-cortical interior, said fractured bone having at least three bone fragments in which first and second fragments have first mating fracture surfaces and second and third bone fragments have second, different mating fracture surfaces, the method comprising attaching one end of a length of flexible cord from within the bone interior to the first bone fragment, attaching an internal pulley bearing said cord from within the bone interior to the second bone fragment, the other end of said cord passing outwardly of the bone through an opening in the third bone fragment, tensioning said cord to draw together said mating fracture surfaces to relieve the fractures, and securing said tensioned cord to said third bone fragment.

4. Method for reducing a bone fracture comprising at least two pairs of bone fragments, a first pair of bone fragments having first mating fracture surfaces and a second pair of bone fragments having second, different mating fracture surfaces, and wherein one bone fragment may be common to each of the first and second pairs, the bone having an exterior cortical portion and an interior non-cortical portion, the method comprising a. attaching one end of a length of flexible cord from the interior of the bone to one fragment of said first pair, said cord extending through an opening in the other bone fragment of said first pair in a direction so that when said cord is placed in tension, the first mating fracture surfaces are drawn toward each other;

b. attaching one end of a second length of flexible cord from the interior of the bone to one fragment of said second pair, said second length of cord extending through an opening in the other bone fragment of said second pair in a direction so that when said cord is placed in tension, the second mating fracture surfaces are drawn toward each other; and c. appropriately adjusting tension in said cords with respect to each other to reduce the fracture surfaces.

5. The method of claim 4 including the step of securing the tensioned cords to said other bone fragments.

6. Method for reducing a bone fracture of a bone having a cortical exterior portion and a non-cortical interior, the fracture comprising at least three bone fragments each having fracture surfaces mating with fracture surfaces of the other fragments, the method comprising:

a. attaching from the interior of the bone to each of two of said bone fragments fastener having an interior pulley surface over which is trained a length of flexible cord;
   b. drawing said cord through an opening in a third bone fragment and tensioning said cord to draw said fracture surfaces together; and
   c. securing said cord to said third bone fragment to respect to each other to reduce the fracture surfaces.

7. Method for reducing a bone fracture of an elongated bone having a medullary canal and a generally transverse fracture dividing the bone into first and second bone fragments, comprising a. attaching from the interior of the bone to one of said bone fragments an internal fastener from which extends at least two flexible, inelastic cord lengths;
   b. drawing said cord lengths through openings formed in said second bone fragment at spaced positions along the interior of the medullary canal of that fragment so that said cord lengths are spaced from one another within the medullary canal at the fracture site; and
   c. securing said cords to said second bone fragment to reduce the fracture surfaces, said spaced cords resisting bending moments at the fracture site.

8. A bone fracture reduction system for use in reducing a fracture of a long bone producing first and second bone fragments, comprising an internal fastener having a threaded portion adapted to be screwed into one bone fragment, a pair of flexible, inelastic cords attached at laterally spaced points to and extending from said internal fastener, and a pair of spaced external fasteners attachable to the other of said bone fragments and having openings through which said cords may respectively pass on opposite sides of the medullary canal, whereby said cords may traverse the fracture site within the medullary canal on opposite sides thereof to resist bending moments at the fracture site.

9. An orthopedic fixation system for fixing a bone having an exterior cortical portion and a non-cortical interior to an element which is a prosthesis or a bone fragment, comprising a length of inelastic, flexible cord; a first fastener for attaching the cord to said element, a second fastener for attaching the cord to the bone to enable the cord to extend from said first fastener within the non-cortical interior of the bone to the second fastener, at least one of said fasteners including an opening through which said cord may pass from the interior of the bone to the exterior, said at least one fastener including a lock for locking the cord to the fastener through which it passes, and at least one of said fasteners includes a threaded portion adapted to be screwed into bone.

10. An orthopedic fixation system for fixing a bone having an exterior cortical portion and a non-cortical interior to a bone fragment resulting from a fracture of said bone, comprising a length of inelastic, flexible cord; a first fastener including a threaded portion adapted to be screwed into bone for attaching the cord to said bone fragment, a second fastener for attaching the cord to the bone to enable the cord to extend from said first fastener within the non-cortical interior of the bone to the second fastener, at least one of said fasteners including a bone plate adapted to engage a bone surface.

11. An orthopedic fixation system for fixing a bone having an exterior cortical portion and a non-cortical interior to a bone fragment resulting from a fracture of said bone, comprising a length of inelastic, flexible cord; a first fastener for attaching the cord to said element, a second fastener for attaching the cord to the bone and enabling the cord to extend from said first fastener within the non-cortical interior of the bone to the second fastener, at least one of said fasteners including an at least partially threaded bore through which said cord may pass from the interior of the bone to the exterior, said at least one fastener including a lock for locking the cord to the fastener through which it passes, said lock comprising a threaded member threadingly received in the bore and capable of engaging said cord to restrain cord movement.

12. A bone fracture reduction system for reducing and promoting healing of a bone fracture of a bone normally having an exterior cortical portion and a non-cortical interior and having bone fragments with generally confronting fracture surfaces, an internal fastener including a threaded portion adapted to be screwed into bone and attachable from within said interior to a first bone fragment, a length of flexible, inelastic cord extendable within said bone interior and attached to said internal fastener and adapted to pass outwardly through an opening in a second bone fragment, said internal fastener and cord being positionable to draw respective fracture surfaces together to reduce said fracture upon tensioning of the cord, said second fastener including a plate adapted to engage the outer surface of the cortical portion.

13. A bone fracture reduction system for reducing and promoting healing of a bone fracture of a bone normally having an exterior cortical portion and a non-cortical interior and having bone fragments with generally confronting fracture surfaces, an internal fastener attachable from within said interior to a first bone fragment, a length of flexible, inelastic cord extendable within said bone interior and attached to said internal fastener and adapted to pass outwardly through an opening in a second bone fragment, said internal fastener and cord being positionable to draw respective fracture surfaces together to reduce said fracture upon tensioning of the cord extendable outwardly through said opening, said system including a second fastener fastenable from the interior of said bone to a third bone fragment, each said fastener having a pulley surface over which said cord is trained to enable the direction of said cord to be changed within the interior of said bone.

14. Method for positioning fragments of a bone fracture with respect to each other to reduce the fracture and promote healing of a bone which normally has an exterior cortical portion and a non-cortical interior, the bone fragments having confronting fracture surfaces forming a fracture interface, the method comprising attaching from within the interior of the bone to a first bone fragment an internal fastener to which is attached a length of flexible, inelastic cord, drawing said cord through a bore formed in a second bone fragment to draw said fragments together in a direction to relieve the fracture, said internal fastener having a threaded end, the method including the step of screwing said threaded end from the interior of said bone into a cortical portion of said first bone segment.

15. Method for positioning fragments of a bone fracture with respect to each other to reduce the fracture and promote healing of a bone which normally has an exterior cortical portion and a non-cortical interior, the bone fragments having confronting fracture surfaces forming a fracture interface, the method comprising attaching from within the interior of the bone a plurality of internal fasteners to different ones of a plurality of bone fragments, said internal fasteners having attached to them a length of flexible, inelastic cord, drawing said cord through a bore formed in a bone fragment and at least one of said internal fasteners including a threaded portion screwed into bone, said internal fasteners being so positioned with respect to each other that when said cord is tensioned, said fragments are drawn together in directions to reduce the fracture.

16. The method of claim 15 wherein at least one of said interior fasteners includes a pulley surface over which said cord is movably trained to change the direction of said cord within the interior of said bone, the method including the step of pulling said cord over said pulley surface.

17. The method of claim 15 wherein each of said interior fasteners includes a pulley surface over which said cord is movably trained to change the direction of said cord within the interior of said bone, the method including the step of pulling said cord over said pulley surfaces.

* * * * *